US011565094B2

United States Patent
Farina et al.

(10) Patent No.: US 11,565,094 B2
(45) Date of Patent: Jan. 31, 2023

(54) DELIVERY DEVICES

(71) Applicant: THE METHODIST HOSPITAL SYSTEM, Houston, TX (US)

(72) Inventors: Marco Farina, Houston, TX (US); Andrea Ballerini, Houston, TX (US); Daniel W. Fraga, Houston, TX (US); Usha Ramachandran Thekkedath, Houston, TX (US); Omaima M. Sabek, Bellaire, TX (US); Ahmed Osama Gaber, Houston, TX (US); Alessandro Grattoni, Houston, TX (US)

(73) Assignee: THE METHODIST HOSPITAL SYSTEM, Houston, TX (US)

(*) Notice: Subject to any disclaimer, the term of this patent is extended or adjusted under 35 U.S.C. 154(b) by 0 days.

(21) Appl. No.: 16/756,938

(22) PCT Filed: Oct. 17, 2018

(86) PCT No.: PCT/US2018/056203
§ 371 (c)(1),
(2) Date: Apr. 17, 2020

(87) PCT Pub. No.: WO2019/079384
PCT Pub. Date: Apr. 25, 2019

(65) Prior Publication Data
US 2021/0187260 A1    Jun. 24, 2021

Related U.S. Application Data

(60) Provisional application No. 62/573,339, filed on Oct. 17, 2017.

(51) Int. Cl.
*A61K 9/00* (2006.01)
*A61M 31/00* (2006.01)
(Continued)

(52) U.S. Cl.
CPC ......... *A61M 31/002* (2013.01); *A61K 9/0024* (2013.01); *A61K 45/06* (2013.01);
(Continued)

(58) Field of Classification Search
CPC ...... A61K 35/39; A61K 45/06; A61K 9/0024; A61K 9/4816; A61M 2202/0437;
(Continued)

(56) References Cited

U.S. PATENT DOCUMENTS 4,938,949 A    7/1990   Borch et al.
5,725,854 A    3/1998   Selawry
(Continued)

FOREIGN PATENT DOCUMENTS

EP    2467150    6/2012
EP    2597148    5/2013
(Continued)

OTHER PUBLICATIONS

Huang et al. (PLoS ONE 2013;8(9):5 pages). (Year: 2013).*
(Continued)

*Primary Examiner* — Ernst V Arnold
(74) *Attorney, Agent, or Firm* — Womble Bond Dickinson (US) LLP

(57) ABSTRACT

Disclosed herein are devices for use in transplanting cells. The devices can include a housing defining a cavity; and a support structure separating the cavity into a cell chamber and a reservoir chamber, wherein the support structure comprises a membrane for fluid communication between the cell chamber and reservoir chamber. The cell chamber can define a first opening comprising a microstructure containing an array of micro-channels, each having a diameter to facilitate growth of vascular tissues; and an array of micro-reservoirs, each having a diameter to facilitate housing of cell aggregates individually. The membrane can define a
(Continued)

surface area that is at least 50% of a total surface area of the support structure. Methods of treating a subject for a disease condition, such as diabetes, are also disclosed.

14 Claims, 8 Drawing Sheets

(51) Int. Cl.
    *A61K 45/06*     (2006.01)
    *C08L 67/04*     (2006.01)
    *B82Y 5/00*     (2011.01)
    *B82Y 30/00*     (2011.01)

(52) U.S. Cl.
    CPC ...... *C08L 67/04* (2013.01); *A61M 2202/0437* (2013.01); *B82Y 5/00* (2013.01); *B82Y 30/00* (2013.01)

(58) Field of Classification Search
    CPC ....... A61M 31/002; A61M 37/00; A61P 3/10; B82Y 30/00; B82Y 5/00; C08L 67/04; F16F 15/1338; F16F 15/134
    See application file for complete search history.

(56) References Cited

U.S. PATENT DOCUMENTS

| | | | |
|---|---|---|---|
| 9,526,880 | B2 | 12/2016 | So et al. |
| 2005/0031689 | A1 | 2/2005 | Shults |
| 2010/0152699 | A1 | 6/2010 | Ferrari et al. |
| 2012/0171292 | A1 | 7/2012 | Sailor |
| 2012/0251587 | A1 | 10/2012 | Van Apeldoorn et al. |
| 2013/0131628 | A1 | 5/2013 | Grattoni et al. |
| 2013/0211368 | A1 | 8/2013 | Martin et al. |
| 2014/0342015 | A1 | 11/2014 | Murphy |
| 2015/0125507 | A1 | 5/2015 | Chen et al. |
| 2015/0209479 | A1 | 7/2015 | Hasilo et al. |
| 2015/0299631 | A1* | 10/2015 | Prabhakarpandian ...................... C12M 21/08 435/29 |
| 2016/0324642 | A1 | 11/2016 | Maria De Peppo |
| 2017/0072074 | A1 | 3/2017 | Gladnikoff et al. |

FOREIGN PATENT DOCUMENTS

| | | |
|---|---|---|
| EP | 2597148 A1 | 5/2013 |
| WO | 2007/070660 | 6/2007 |
| WO | 2010056986 | 5/2010 |
| WO | 2010120817 | 10/2010 |
| WO | 2013112734 | 8/2013 |
| WO | 2014/184673 | 11/2014 |
| WO | 2016187100 | 11/2016 |
| WO | 2017/156026 | 9/2017 |

OTHER PUBLICATIONS

Allard et al., Local delivery of ferrociphenol lipid nanocapsules followed by external radiotherapy as a synergistic treatment against intracranial 9L glioma xenograft. Pharm Res, 2010. 27(1): p. 56-64.
Ansari et al. Radiofrequency ablation or percutaneous ethanol injection for the treatment of liver tumors. World J Gastroenterol, 2012. 18(10): p. 1003-8.
Brennan, Daniel C., et al. Long-term follow-up of the edmonton protocol of islet transplantation in the United States. American Journal of Transplantation 16.2 (2016): 509-517.
Buitinga, Mijke, et al. Coculturing human islets with proangiogenic support cells to improve islet revascularization at the subcutaneous transplantation site. Tissue Engineering Part A 22.3-4 (2016): 375-385.
Chonan et al. CD40/CD40L expression correlates with the survival of patients with glioblastomas and an augmentation in CD40 signaling enhances the efficacy of vaccinations against glioma models. Neuro Oncol. 2015, 17(11), 1453-62.
Cosentino et al. Dynamic Model of Bimolecular Diffusion through Two-Dimensional Nanochannels. J Phys Chem B 2005, 109, 7358-7364.
Desai, Tejal, and Lonnie D. Shea. Advances in islet encapsulation technologies. Nature reviews Drug discovery 16.5 (2017): 338-350.
Diop-Frimpong et al. Losartan inhibits collagen I synthesis and improves the distribution and efficacy of nano therapeutics in tumors. Proceedings of the National Academy of Sciences. 108, 2909-2914 (2011).
Dong, et al., Intratumoral delivery of beta-lapachone via polymer implants for prostate cancer therapy. Clin Cancer Res, 2009. 15(1): p. 131-9.
Dubrot et al., Intratumoral injection of interferon-alpha and systemic delivery of agonist anti-CD137 monoclonal antibodies synergize for immunotherapy. Int J Cancer, 2011. 128(1): p. 105-18.
Farina, Marco, et al. 3D printed vascularized device for subcutaneous transplantation of human islets. Biotechnology Journal 12.9 (2017): 1700169.
Ferrati et al. Delivering enhanced testosterone replacement therapy through nanochannels. The journal of sexual medicine. 2015, 4(3), 446-251.
Ferrati et al. The nanochannel delivery system for constant testosterone replacement therapy. The journal of sexual medicine. 2015, 12(6), 1375-1380.
Ferrati et al., Leveraging nanochannels for universal, zero-order drug delivery in vivo. J Control Release, 2013. 172(3): p. 1011-9.
Fine et al., A robust nanofluidic membrane with tunable zero-order release for implantable dose specific drug delivery. Lab Chip, 2010. 10(22): p. 3074-83.
Fine, Daniel, et al. Silicon micro-and nanofabrication for medicine. Advanced healthcare materials 2.5 (2013): 632-666.
Fuso Nerini et al. Instratumor heterogeneity and its impact on drug distribution and sensitivity. Clinical Pharmacology & Therapeutics. 96, 224-238 (2014).
Gerloni et al. Functional cooperation between T helper cell determinants. Proc Natl Acad Sci USA. 97, 13269-74 (2000).
Goldberg et al., Intratumoral cancer chemotherapy and immunotherapy opportunities for nonsystemic preoperative drug delivery. Journal of Pharmacy and Pharmacology, 2002. 54(2): p. 159-180.
Grattoni et al. Device for Rapid and Agile Measurement of Diffusivity in Micro- and Nanochannels. Anal Chem. 83, 3096-103 (2011).
Grattoni et al. Gated and near-surface diffusion of charged fullerenes in nanochannels. ACS nano. 5, 9382-9391 (2011).
Grattoni et al., Nanochannel technology for constant delivery of chemotherapeutics beyond metronomic administration. Pharm Res, 2011. 28(2): p. 292-300.
Grattoni, A., Biomedical Engineering Seminar Series: Nanotechnologies for Patient Care, TAMU Seminar, accessed 2017.
Gu, Bon Kang, et al. 3-dimensional bioprinting for tissue engineering applications. Biomaterials research 20.1 (2016): 12.
Guerin et al., Recent advances in brain tumor therapy: local intracerebral drug delivery by polymers. Invest New Drugs, 2004. 22(1): p. 27-37.
Guo et al., Enhanced 4T1 breast carcinoma anticancer activity by co-delivery of doxorubicin and curcumin with core-shell drug-carrier based on heparin modified poly(L-lactide) grafted polyethylenimine cationic nanoparticles. J Biomed Nanotechnol, 2014. 10(2): p. 227-37.
Hekmat et al. The effects of silver nanoparticles and doxorubicin combination on DNA structure and its antiproliferative effect against T47D and MCF7 cell lines. Journal of biomedical nanotechnology. 8, 968-982 (2012).
Holohan et al., Cancer drug resistance: an evolving paradigm. Nature Reviews Cancer, 2013. 13(10): p. 714-726.
Hood et al., Fiberoptic microneedle device facilitates volumetric infusate dispersion during convection-enhanced delivery in the brain. Lasers Surg Med, 2013. 45(7): p. 418-26.
Hood, R. Lyle, et al. Nanochannel implants for minimally-invasive insertion and intratumoral delivery. Journal of biomedical nanotechnology 12.10 (2016): 1907-1915.

(56) References Cited

OTHER PUBLICATIONS

Hood, R. Lyle, et al. Pioneering medical advances through nanofluidic implantable technologies. Wiley Interdisciplinary Reviews: Nanomedicine and Nanobiotechnology 9.5 (2017): e1455.
Kalyanaraman et al. Doxorubicin-induced apoptosis: Implications in cariotoxicity. Oxygen/Nitrogen Radicals: Cell Injury and Disease, Springer, 2002, pp. 119-214.
Kaufman et al. Local delivery of vaccinia virus expressing multiple costimulatory molecules for the treatment of established tumors. Hum Gene Ther, 2006. 17(2): p. 239-44.
Lau, Joey, et al. Beneficial role of pancreatic microenvironment for angiogenesis in transplanted pancreatic islets. Cell transplantation 18.1 (2009): 23-30.
Lesinski et al., Release of biologically functional interferon-alpha from a nanochannel delivery system. Biomed Microdevices, 2005. 7(1): p. 71-9.
Lesniak et al. Local delivery of doxorubicin for the treatment of malignant brain tumors in rats. Anticancer research. 25, 3825-3831 (2005).
Marabelle et al. Depleting tumor-secific Tregs at a signle site eradicates disseminated tumors. The Journal of clinical investigation. 123, 2447 (2013).
Marabelle et al., Intratumoral immunization: a new paradigm for cancer therapy. Clin Cancer Res, 2014. 20(7): p. 1747-56.
Markovic, Marica, et al. Hybrid tissue engineering scaffolds by combination of three-dimensional printing and cell photoencapsulation. Journal of nanotechnology in engineering and medicine 6.2 (2015).
Martin et al. Tailoring width of microfabricated nanochannels to solute size can be used to control diffusion kinetics. J Control Release 2005; 102(1); 123-33.
Milo et al. BioNumbers—the database of key numbers in molecular and cell biology. Nucleic acids research. 38, D750-D753 (2010).
Mitra et al. Tumour targeted delivery of encapsulated dextran-doxorubicin conjugate using chitosan nanoparticles as carrier. Journal of Controlled Release. 74, 317-323 (2001).
Orlowski et al. Randomized phase III study of pegylated liposomal doxorubicin plus bortezomib compared with bortezomib alone in relapsed or refractory multiple myeloma: combination therepy improves time to progression. Journal of Clinical Oncology. 25, 3892-3901 (2007.
Panchuk et al., Application of C-60 Fullerene-Doxorubicin Complex for Tumor Cell Treatment In Vitro and In Vivo. Journal of Biomedical Nanotechnology, 2015. 11(7): p. 1139-1152.
Patel et al. Low dose rate vs. High dose rate brachytherapy in the treatment of carcinoma of the uterine cervix: A clinical trial. International Journal of Radiation Oncology* Biology* Physics. 1994, 28, 335-341.
Pepper, Andrew R., et al. A prevascularized subcutaneous device-less site for islet and cellular transplantation. Nature biotechnology 33.5 (2015): 518-523.
Piconese et al. OX40 triggering blocks suppression by regulatory T cells and facilitates tumor rejection. J Exp Med. 205, 825-39 (2008).
Rebucci et al. Molecular aspects of cancer cell resistance to chemotherapy. Biochemical pharmacology, 2013. 85(9): p. 1219-1226.
Sabek, Omaima M., et al. Characterization of a nanogland for the autotransplantation of human pancreatic islets. Lab on a chip 13.18 (2013): 3675-3688.
Sabek, Omaima M., et al. Characterization of a nanogland for the autotransplantation of human pancreatic islets. Lab on a chip 13.18 (2013): 3675-3688. Supplementary Information.
Sabek, Omaima M., et al. Three-dimensional printed polymeric system to encapsulate human mesenchymal stem cells differentiated into islet-like insulin-producing aggregates for diabetes treatment. Journal of tissue engineering 7 (2016) 2041731416638198.
Shapiro, AM James, et al. International trial of the Edmonton protocol for islet transplantation. New England Journal of Medicine 355.13 (2006): 1318-1330.
Sharma et al. Controlled-release microchips. Expert Opin Drug Deliv 2006: 3(3): 379-94.
Singh, Saket Kumar, et al. Reloadable silk-hydrogel hybrid scaffolds for sustained and targeted delivery of molecules. Molecular Pharmaceutics 13.12 (2016): 4066-4081.
Smink, Alexandra M., et al. A retrievable, efficacious polymeric scaffold for subcutaneous transplantation of rat pancreatic islets. Annals of surgery 266.1 (2017): 149-157.
Song, Shang, et al. Silicon nanopore membrane (SNM) for islet encapsulation and immunoisolation under convective transport. Scientific reports 6.1 (2016): 1-9.
Toyoizumi, et al., Combined therapy with chemotherapeutic agents and herpes simplex virus type IICP34.5 mutant (HSV-1716) in human non-small cell lung cancer. Human Gene Therapy, 1999, 10(18):17.
Walczak et al. Long-term biocompatibility of NanoGATE drug delivery implant. Nanobiotechnology, 2005, 1, 35-42.
Weinberg et al. Polymer implants for intratumoral drug delivery and cancer therapy. J Pharm Sci, 2008. 97(5): p. 1681-702.
Yapp et al., The potentiation of the effect of radiation treatment by intratumoral delivery of cisplatin. Int J Radiat Oncol Biol Phys, 1998. 42(2): p. 413-20.
Ziemys et al. Hierarchical modeling of diffusive transport through nanochannels by coupling molecular dynamics with finite element method. Journal of Computational Physics. 2011, 230(14), 5722-5731.
International Search Report and Written Opinion issued for Application PCT/US2016/032658, dated Aug. 16, 2016.
International Preliminary Report on Patentability issued for Application No. PCT/US2018/056203, dated Apr. 30, 2020.
International Search Report and Written Opinion in PCT/US2018/056203, dated Jan. 2, 2019. 10 pages.

* cited by examiner

DELIVERY DEVICES

CROSS-REFERENCE TO RELATED APPLICATIONS

This application claims the benefit and priority to and is a United States National Phase Patent Application of International Patent Application Number PCT/US2018/056203, filed on Oct. 17, 2018, which claims priority to U.S. Patent Application No. 62/573,339, filed on Oct. 17, 2017, both disclosures of which are expressly incorporated herein by reference in their entireties.

BACKGROUND

Cell therapy has become an attractive option to treat many medical conditions including diabetes. However, it is associated with several challenges like loss of graft function due to cell dispersion and lack of vascularization, and the need for continuous immunosuppression. In spite of early success with intrahepatic transplantation, widespread use of islet transplantation has been hampered by poor long-term survival of the graft (Brennan D. C. et al., *Am. J. Transplant. Off. J. Am. Soc. Transplant. Am. Soc. Transpl. Surg.* 16(2), 375-730 (2015); Shapiro, A. M. J. et al. *N. Engl. J. Med.* 355, 1318-30 (2006)). After intra-hepatic or intravascular islet transplantation, graft function is lost rapidly due to dispersion of transplanted tissue, damage to graft caused by blood-mediated inflammatory reaction, and the hypoxic stress due to the limited ingrowth of new blood vessels (Lau, J. et al. *Cell Transplant.* 18, 23-30 (2009)). High oxygen demand and the need for physiological architecture necessitate a highly vascularized and three-dimensional system for the long-term survival and function of transplanted islets. Conventional immunosuppressant drugs are systemic, causing unwanted side effects and low dosage at the need site. In addition, a minimally invasive and accessible site is fundamental for implantation, replenishment and graft retrieval. Retrievability is important when using engineered stem cells, whose long term fate and potential for tumor formation are not well known. The present disclosure, including materials, devices, and methods disclosed herein address this and other needs.

SUMMARY

In accordance with the purposes of the disclosed devices, systems, and methods as embodied and broadly described herein, the disclosed subject matter relates to compositions, methods of making said devices and systems, and methods of using said devices and systems. More specifically, disclosed herein are devices comprising a housing containing a perimeter wall defining a cavity; and a support structure separating the cavity into a cell chamber and a reservoir chamber, wherein the cell chamber comprises a first opening comprising a microstructure; wherein the support structure comprises a membrane for fluid communication (for example, diffusion) between the cell chamber and reservoir chamber, and wherein the membrane defines a surface area that is at least 50% of a total surface area of the support structure. The membrane can provide controlled release of an agent from the reservoir chamber to the cell chamber. The housing of the device can be derived from a biocompatible polymer (also referred to herein as a biopolymer), such as polylactic acid, Teflon, or combinations thereof. The devices disclosed herein can have a diameter of at least 8 mm and a thickness of at least 2.5 mm.

The membrane in the device can comprise nano-channels having a diameter from 2.5 nm to 1000 nm. The density of the nano-channels can be greater than 100,000 nano-channels mm$^{-2}$ of the membrane. In some aspects of the device, the surface area of the membrane defines from 50% up to 100% of the total surface area of the support structure.

As described herein, the cell chamber comprises an opening containing a microstructure. The microstructure can comprise an array of micro-channels present on an outer surface of the cell chamber, each having a diameter to facilitate growth of vascular tissues; and an array of micro-reservoirs present on an inner surface of the cell chamber, each having a diameter to facilitate housing of cell aggregates individually. In some embodiments, the cell aggregates can include insulin producing cell aggregates (ILIPAs), mesenchymal stem cells, Leydig cells, pancreatic islets, or a combination thereof. In further embodiments, the cell aggregates can include cells that release hormones. The cell aggregates can, in other embodiments, include human embryonic stem cells (hESCs) and pluripotent stem cells (iPSCs) differentiated to obtain insulin producing cells, adult somatic cells, hepatocytes, fibroblasts, kidney cells (e.g., genetically engineered to secrete human ciliary neurotrophic factor). Each micro-channel of the cell chamber can have a diameter of 100 µm or less. Each micro-reservoir can have a diameter of from 100 to 300 µm. In certain embodiments, each micro-reservoir is in fluid communication with at least two micro-channels.

The reservoir chamber can comprise one or more second openings. The openings in the cell chamber and/or reservoir chamber provide for refilling the cell chamber and/or the reservoir chamber with a cell aggregate or a bioactive agent (such as an immunosuppressant drug), respectively. In some embodiments, the second openings can be sealed with silicone, plastic, or rubber.

Methods of treating a subject for a disease condition, such as diabetes, are also disclosed. The method can include implanting a device as disclosed herein in the subject, incubating the device until the device is infiltrated with vascular tissues; and injecting insulin producing cells into the cell chamber of the device. In some embodiments, the cell chamber of the device comprises a growth factor, such as vascular endothelial growth factors to stimulate vascularization. The method can further comprise injecting an immunosuppressant drug in the reservoir chamber of the device.

Additional advantages will be set forth in part in the description that follows or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects described below.

FIG. 2A shows a vascularized cell chamber comprising cells. FIG. 2B shows a magnified view of the micro-reservoirs and micro-channels in a cell chamber. FIG. 2C shows an exemplary cell chamber. FIGS. 2D and 2E show SEM images of the micro-reservoirs and micro-channels from FIG. 2D.

FIG. 4A shows the structure of the cell chamber. FIG. 4B shows the structure of the micro-reservoirs (IR) and micro-channels (µCH) in the cell chamber. FIGS. 4C and 4D are magnification of the micro-channels under SEM. FIG. 4E shows PLA superficial roughness measurements after argon and oxygen plasma treatments as a function of changing time of application (0, 30, 90, 120, and 150 seconds). FIG. 4F shows AFM pictures of PLA surface treated with oxygen plasma after 0, 90 and 120 seconds. Average and SEM are represented. **p<0.01

FIGS. 5A-5I show tissue response at the device-subcutaneous tissue interface. Different concentrations of VEGF were tested and the device was retrieved after 1, 2, and 4 weeks from the implantation. Diffuse spots of calcification (black arrows) were present at week 4 with the highest VEGF concentration in FIG. 5I. FIGS. 5J-5L show CD31 staining of tissue. Scale bar is 50 µm. FIG. 5M shows the average and SEM of the CD31 count for high power field. FIGS. 5N-5O show representative optical microscope visualization of the tissue collected from the device reservoir (VEGF 0.5 µg/mL group), showing the presence of mature vessels. Dotted lines represent device-subcutaneous tissue interface and the black arrows follow the path of a vessel through the polymeric scaffold. FIGS. 5P-5Q show neurofilament staining (SMI312-R, in green) indicating the proximity of subcutaneous nerve bundles to the encapsulation device.

FIGS. 6B-6C show basal blood glucose levels (FIG. 6B) and body weight (FIG. 6C) over time. Average and SEM are represented. *p<0.05; ***p<0.001.

FIG. 7A is a T1-weighted image, and FIG. 7B is a T2-weighted image. The rings depict the estimated implant location. FIG. 7C provides a depiction of the visible contrast threshold as concentration diminishes exponentially as Magnevist diffuses away from the implant reservoir. Unmeasurably quick signal response time rendered volumes with high Magnevist concentration as voids.

FIG. 8A shows an optical image if a 3D printed and assembled NICHE device and component parts. FIG. 8B shows a 3D rendering of the NICHE device, sectioned and exploded. FIG. 8C provides a SEM image of nylon membrane. FIG. 8D shows the cell reservoir microchannels.

DETAILED DESCRIPTION

Figure 1A:
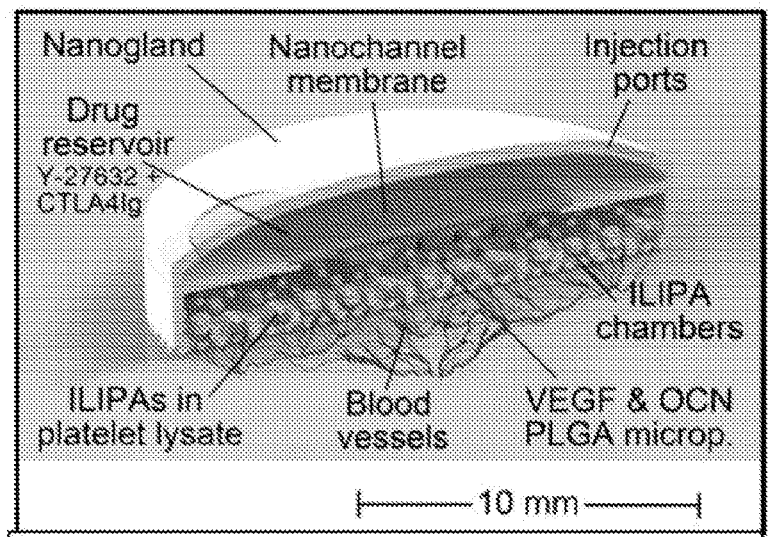
FIGS. 1A-1B are images showing a cross-section of exemplary cell transplantation device comprising a cell chamber and a drug reservoir chamber.

The devices, systems, and methods described herein may be understood more readily by reference to the following detailed description of specific aspects of the disclosed subject matter and the Figures and Examples included therein.

Before the present devices, systems, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a micro-channel" includes mixtures of two or more such micro-channels, reference to "an opening" includes two or more such openings, reference to "the drug" includes mixtures of two or more such drugs, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., the effects of diabetes). It is understood that this is typically in relation to some standard or expected value, in other words it is relative, but that it is not always necessary for the standard or relative value to be referred to.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as diabetes), stabilized (i.e., not worsening) state of diabetes, preventing or delaying symptoms of diabetes, delay or slowing of diabetes progression, amelioration of the diabetic state.

The term "patient" preferably refers to a human in need of treatment with for example, insulin or treatment for any purpose, and more preferably a human in need of such a treatment to treat diabetes, or a diabetic condition. However, the term "patient" can also refer to non-human animals, preferably mammals such as dogs, cats, horses, cows, pigs, sheep and non-human primates, among others, that are in need of treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, the term "device" is intended to encompass a product comprising the specified components, as well as any product which results, directly or indirectly, from combination of the specified components in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

Devices

Transplantation of islets on porous biomaterials has emerged as a promising strategy for long-term islet function facilitating rapid tissue ingrowth, vascularization and innervation providing oxygen, nutrition, and waste removal. Disclosed herein are cell encapsulation devices and systems that can be used for transplantation of cells, including islet. The devices disclosed herein can maintain pancreatic islets close to blood vessels in a growth factor enriched environment, but separated from each other to mimic the physiological architecture in the pancreas and avoid cell crowding.

Figure 1B:
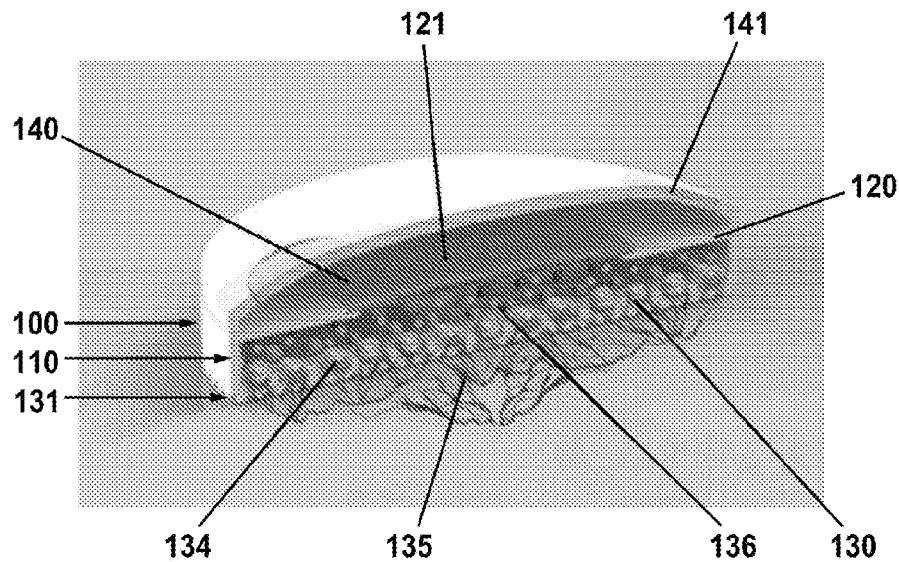

FIGS. 1A-1B are images showing a cross sectional view of an exemplary embodiment of a cell encapsulation device 100. The device 100 can include a housing 110 comprising a perimeter wall defining a cavity. The cavity can be separated by a support structure 120 to form a first chamber (also referred to herein as a cell chamber or cell reservoir 130), a second chamber (also referred to herein as a reservoir chamber or drug reservoir 140). The support structure (also referred to herein as a membrane holder, 120) can include a membrane 121 for fluid communication between the cell chamber 130 and reservoir chamber 140. FIGS. 8A-8D are also images showing a cross sectional view of an exemplary embodiment of a cell encapsulation device.

The device can have any configuration or shape appropriate for maintaining biological activity and providing access for delivery of a cell or function, including for example, cylindrical, rectangular, disc-shaped, square-shaped, ovoid, stellate, or spherical. Moreover, the device can be coiled or tubular. In cases where the device is to be retrieved at some time after it is implanted, configurations which tend to lead to migration of the devices from the site of implantation (such as spherical devices small enough to travel in the recipient's blood vessels) should be avoided. As noted herein, all or portions of the device can be formed from a 3D printer. Thus the shape can be highly complex and irregular, depending on the particular payload and location of use. Preferably, the device can be configured to offer high structural integrity and are easy to retrieve from the host. In some specific examples, the device is flexible so that it can be easily maneuvered (implanted and removed).

The dimensions of the device can be varied depending on the contents of the chambers, the volume of the chambers, the intended use, and the like. For example, the dimensions of the device can permit serial implantation throughout a tissue volume via a minimally-invasive, trocar delivery mechanism. The dimensions can also be established to fit into a specific location in a subject. In some examples, the dimensions of the device can be configured for holding 3,000 or more islets (e.g., 4,000 or more or 5,000 or more islets). There are no strict requirements for the device dimensions and can be ultimately tailored to match the size of commercially available deployment systems already adopted in the clinics.

In some examples, the device can have a diameter of less than 25 mm, e.g., 22 mm or less, 20 mm or less, 18 mm or less, 17 mm or less, 16 mm or less, 15 mm or less, 14 mm or less, 13 mm or less, or 12 mm or less. In other examples, the device can have a diameter of 8 mm or greater, e.g., 9 mm or greater, 10 mm or greater, 11 mm or greater, 12 mm or greater, 13 mm or greater, 14 mm or greater, 15 mm or greater, 16 mm or greater, 18 mm or greater, 20 mm or greater, 22 mm or greater, or 25 mm or greater. In certain embodiments, the device can have a diameter of from 8 mm to 25 mm, from 10 mm to 25 mm, from 12 mm to 25 mm, or from 12 mm to 20 mm.

The height (or thickness) of the device can be less than 8 mm, e.g., 7 mm or less, 6 mm or less, 5 mm or less, 4.5 mm or less, or 3 mm or less. In other examples, the device can have a height (thickness) of 2.5 mm or greater, e.g., 3 mm or greater, 3.5 mm or greater, 4 mm or greater, 4.5 mm or greater, 5 mm or greater, or 6 mm or greater. In certain embodiments, the device can have a height (thickness) of from 2.5 mm to 8 mm, from 3 mm to 8 mm, from 3 mm to 6 mm, or from 3.5 mm to 5 mm.

In some examples, when the device does not have a circular shape and diameter, the device can have a longest linear dimension of less than 25 mm, e.g., 22 mm or less, 20 mm or less, 18 mm or less, 17 mm or less, 16 mm or less, 15 mm or less, 14 mm or less, 13 mm or less, or 12 mm or less. In other examples, the device can have a longest linear dimension of 8 mm or greater, e.g., 9 mm or greater, 10 mm or greater, 11 mm or greater, 12 mm or greater, 13 mm or greater, 14 mm or greater, 15 mm or greater, 16 mm or greater, 18 mm or greater, 20 mm or greater, 22 mm or greater, or 25 mm or greater. In certain embodiments, the device can have a longest linear dimension of from 8 mm to 25 mm, from 10 mm to 25 mm, from 12 mm to 25 mm, or from 12 mm to 20 mm Housing The housing (body) of the device can be fabricated from a material that is biologically acceptable, e.g., does not illicit an immune response. Various polymers and polymer blends can be used to manufacture the device, including, biodegradable or non-biodegradable materials. The device housing is preferably fabricated from a hydrophilic, viscoelastic, and/or biocompatible material. However, other materials can be used to fabricate the device and the surface of the device subsequently surface treated with a material that is hydrophilic, viscoelastic, and/or biocompatible. In specific examples, the device is surface treated with a biomaterial.

Examples of suitable polymers for fabricating the device include polylactic acids (PLA), polyalkylenes (including polypropylene and polyethylene), poly(alkylene glycols), polycarbonate (PC), cyclic olefin polymer (COP), poly(trimethylene carbonate), polycaprolactone (PCL), poly(lactic-co-glycolic acid) (PLGA), polyacrylates (including acrylic copolymers), polyacrylonitrile, polyvinylidenes, polyvinyl chloride copolymers, polyurethanes, polystyrenes, polyimides, polyamides, polyethyleneimine, cellulose polymers (including cellulose acetates and cellulose nitrates), polysulfones (including polyethersulfones), polyesters, polyphosphazenes, polyacrylonitriles, poly(acrylonitrile/co-vinylchloride), poly(vinylsiloxane), as well as derivatives, copolymers and mixtures of the foregoing. Additional examples that may be used include tetrafluoroethylene/polytetrafluoroethylene (PTFE; also known as Teflon®), ePTFE (expanded polytetrafluoroethylene), hydroxylpropyl methyl cellulose (HPMC), methacrylate polymers, poly(ethylene glycol), poly(ethyl ethacrylate), polyhydroxyvalerte, polyhydroxybutyrate, polydiaxanone, polyanhydrides, polycyanocrylates, poly(amino acids), poly(orthoesters), copolymer of polyalkylene glycol, terephthalate, collagen, gelatin, chitosans, fibronectin, extracellular matrix proteins, vinculin, agar, agarose, and alginates or combinations thereof. One specific example of a suitable polymer is vicryl.

Figures 4A, 4B, 4C, 4D, 4E, 4F:
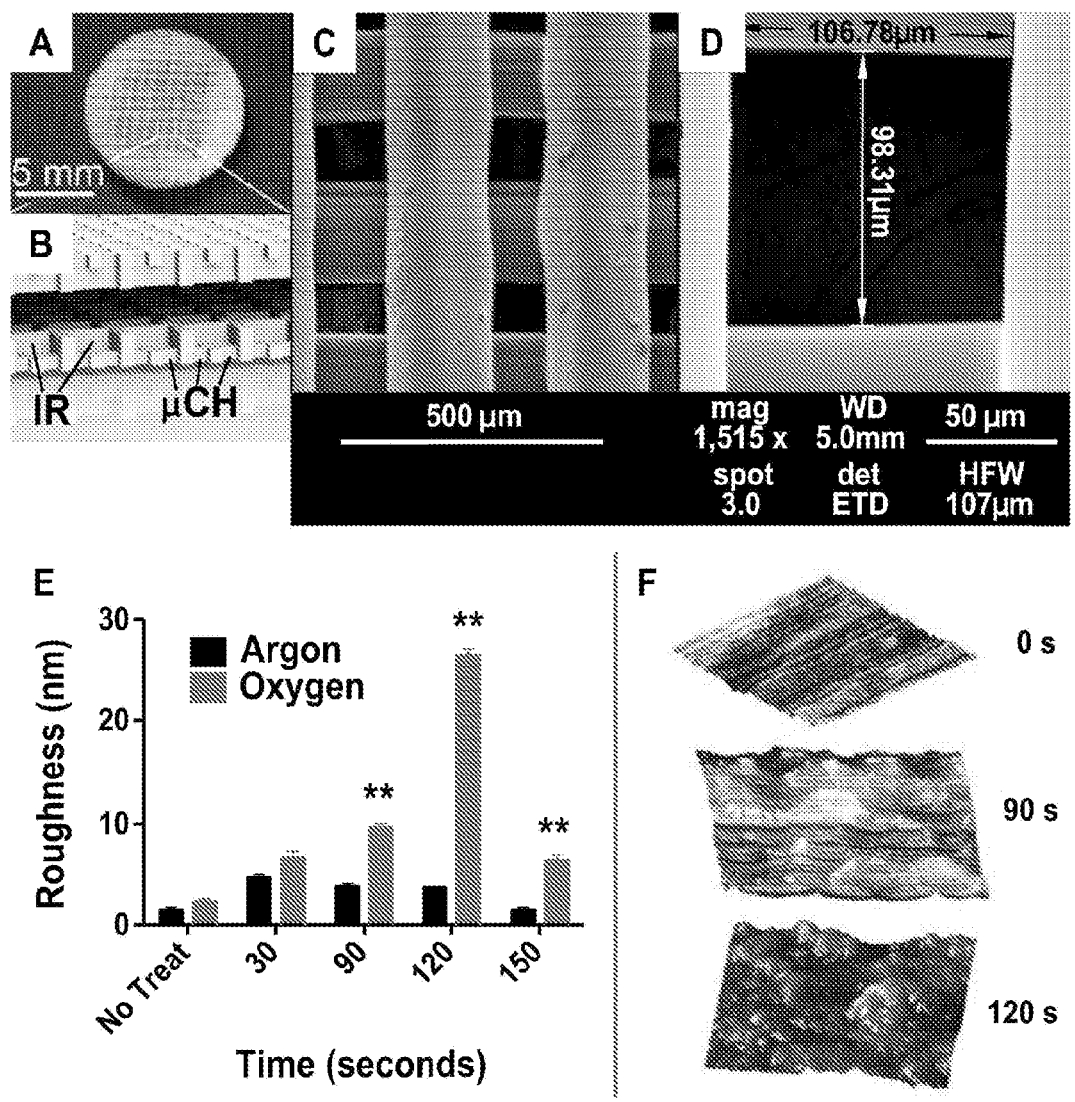
FIGS. 4A-4F shows a mouse prototype of the cell chamber.

In specific examples, the housing can be fabricated from polylactic acid (PLA). PLA is a widely adopted polymer in biomedical devices, biocompatible, and presents good elasticity and mechanical strength suitable for subcutaneous implantation. However, due to the chiral nature of lactic acid, PLA is hydrophobic and may exhibit low cell adhesion properties. In certain embodiments, the device including a hydrophobic polymer such as PLA can be surface treated with plasma to improve the low surface free energy as well as modify the surface's wettability, surface roughness, and surface chemistry. For example, plasma activation can increase the surface's free energy forming a broad variety of functional groups on the surface, including polar groups, which can significantly change wettability and have a desirable effect on material-cell interactions. FIG. 4E show oxygen and argon plasma treatments increased surface roughness. It has been shown that the oxygen treatment causes deeper patterns, which has been demonstrated to be beneficial for cell attachment and proliferation.

First Chamber (Cell Chamber)

As described herein, the devices can include a first chamber (also referred to herein as the cell chamber) for housing the transplanted cells. The cell chamber includes an opening (also referred to herein as the first opening), which can be located distal to the membrane separating the cell chamber and the drug reservoir. The opening in the cell chamber can be of a "semi-permeable" nature to permit for example, molecules produced by the cells to diffuse from the device into the surrounding host tissue, as well as vascular tissue to grow into the first chamber. In some embodiments, the opening in the cell chamber can include a microstructure.

FIGS. 2A-2E are images of an exemplary embodiment of the cell chamber 130 comprising a microstructure 131. On the inner surface of the microstructure 131 can comprise an array of micro-reservoirs 132, and the outer can comprise an array of micro-channels 133. The array of micro-reservoirs 132 can be configured to house the transplanted cells 134. Preferably, the micro-reservoirs 132 are configured to house the cells 134 individually while maintaining them in close proximity and avoiding clustering. In some examples, the micro-reservoirs 132 can be laterally connected to each other and separated by cell-free zones.

The size of the micro-reservoirs 132 are selected to provide an optimal surface area to volume ratio for holding cells and for ensuring long-term survival of the cells within the vascularized cell chamber. In some embodiments, the size of the micro-reservoirs 132 can be 50 microns or greater. For example, the size of the micro-reservoirs 132 can be 100 microns or greater, 125 microns or greater, 150 microns or greater, 175 microns or greater, 200 microns or greater, 225 microns or greater, 250 microns or greater, or 275 microns or greater. In some embodiments, the size of the micro-reservoirs 132 can be 500 microns or less, 450 microns or less, 400 microns or less, 350 microns or less, 300 microns or less, 275 microns or less, 250 microns or less, 225 microns or less, 200 microns or less, 175 microns or less, 150 microns or less, or 100 microns or less. In certain embodiments, the size of the micro-reservoirs 132 can be from 50 microns to 500 microns, from 100 microns to 400 microns, or from 100 microns to 300 microns.

The number of micro-reservoirs 132 in the cell chamber can be determined based on the volume and/or number of cells that are to be transplanted. In some embodiments, the total volume of the cell chamber 130 can be adjusted by increasing or decreasing the number of micro-reservoirs 132 while maintaining an optimum surface area to volume ratio of each individual micro-reservoirs 132. In other embodiments, the cell chamber can comprise a fixed number of micro-reservoirs 132, but only a selected number of micro-reservoirs 132 may be infused with cells depending on the total volume requirement of the device.

In some aspects of the device, the cell chamber can comprise a sufficient number of micro-reservoirs to house an adequate human dosage of islets to treat and ameliorate a subject with diabetes once implanted. For example, the cell chamber can comprise a sufficient number of micro-reservoirs to house 1,000 or greater, 2,000 or greater, 3,000 or greater, 4,000 or greater, or 5,000 or greater islets. Ultimately, number of micro-reservoirs can vary as the cell loading density varies. The size and shape of the micro-reservoirs can likewise vary depending on the needs of the recipient. The number of cells loaded into any device will depend on the dosage contemplated or dosage mandated by the treatment and the number of devices employed in the treatment.

The micro-reservoirs 132 are connected to the outside (for example, surrounding tissues when implanted in a subject) by an array of micro-channels 133. The micro-channels 133 are configured to allow micro-vessels (for example, transmembrane blood vessels, 135) to enter the device and be maintained as robust, healthy vessels, which is important for the survival and normal functioning of the cells 134 infused into the device. Ingrown tissues also stabilize the implant and prevent inadvertent movement of the device in situ.

The size of the micro-channels 133 can be selected to facilitate vascularization within the cell chamber of the device. In some embodiments, the size of the micro-channels 133 can be selected to exclude immune cells or immune agents from penetrating the implanted device. In some other embodiments, the size of the micro-channels 133 does not necessarily need to exclude immune cells or immune agents from infiltrating the device.

In some embodiments, the size of the micro-channels 133 can be less than 200 microns.

For example, the size of the micro-channels 133 can be 170 microns or less, 150 microns or less, 125 microns or less, 100 microns or less, 90 microns or less, 80 microns or less, 70 microns or less, 60 microns or less, 50 microns or less, 40 microns or less, 30 microns or less, or 20 microns or less. In some embodiments, the size of the micro-channels 133 can be 10 microns or greater, 20 microns or greater, 30 microns or greater, 40 microns or greater, 50 microns or greater, 60 microns or greater, 70 microns or greater, 80 microns or greater, 90 microns or greater, 100 microns or greater, 125 microns or greater, 150 microns or greater, or 175 microns or greater. In certain embodiments, the size of the micro-channels 133 can be from 10 microns to 200 microns, or from 20 microns to 200 microns. In another embodiment, the size of the micro-channels 133 can be 40 microns.

Each micro-reservoir 132 can be physically contacting one or more micro-channels 133. For example, each micro-reservoir can be physically contacting one or more, two or more, three or more, four or more, five or more micro-channels. In specific examples, each micro-reservoir can be physically contacting two or more micro-channels.

The micro-reservoirs and/or micro-channels (including adjacent micro-reservoirs and/or micro-channels) can take on different designs, volume capacity, cross-sectional dimensions and surface areas.

The cell chamber can include a loading port (not shown) for cell loading. The loading port can be included in the microstructure or part of the device itself. The loading port can be on the top or side of the device. In some embodiments, the loading port can be an opening sealed with a plastic, rubber, or silicone. The payload can be filled into the cell chamber through the loading port and then sealed. In some embodiments, the size of the loading port can be from 0.5 mm to 3 mm, from 0.5 mm to 2 mm, or from 1 mm to 2 mm.

The cell chamber 130 can further comprise a biological or non-biological agent to stimulate tissue incorporation and angiogenesis, for example, growth factors 136. Examples of biological or non-biological agents to stimulate tissue incorporation and angiogenesis include but are not limited to: VEGF (vascular endothelial growth factor), PDGF (platelet derived growth factor), FGF1 (fibroblast growth factor), NRP1 (neuropilin1), Ang1, Ang2 (angiogenin 1,2), TGFβ/endoglin, MCP1, αvβ3, αvβ5, CD31, VE-cadherin, ephrin, plasminogen activators, angiogenin, Dell, aFGF (acid fibroblast growth factor), vFGF (basic fibroblast growth factor), follistatin, GCSF (granulocyte colonystimulating factor), HGF (hepatocyte growth factor), Il8 (interleukin8), Leptin, midkine, placental growth factor, PDECGF (platelet derived endothelial growth factor), PTN (pleiotrophin), progranulin, proliferin, TGFα, and TNFα.

The cell chamber can be considered to have a total height or thickness determined by a dimension that extends vertically from the support structure (that separates the cell chamber and drug chamber) to an outer surface of the micro-channel. In some embodiments, the thickness of the cell chamber can be less than 5 mm, e.g., 4.5 mm or less, 4 mm or less, 3.5 mm or less, or 3 mm or less. In other examples, the thickness of the cell chamber can be 2.0 mm or greater, e.g., 2.5 mm or greater, 3 mm or greater, 3.5 mm or greater, or 4 mm or greater. For example, the thickness of the cell chamber can be from 2.0 mm to 5 mm or from 2.5 mm to 5 mm Second Chamber (Reservoir Chamber/Drug Reservoir)

As described herein, the devices can include a second chamber (also referred to herein as the reservoir chamber or drug chamber). The reservoir chamber can be used as a drug delivery vehicle. For example, a major challenge in transplantation is the induction of donor specific tolerance. A localized delivery of immunomodulatory drugs in the vicinity of transplanted tissue, which will protect the transplant from immune rejection and at the same time eliminate the adverse effects associated with systemic immunosuppression, is the ideal choice in islet/beta cell transplantation. The disclosed reservoir chamber can be configured to provide a constant and sustained delivery of bioactives including immunomodulatory drugs to the cells in the cell chamber. Examples of immunomodulatory drugs can include corticosteroids, cytostatics, calcineurin inhibitors, and some antibodies. Specific examples of immunomodulatory drugs include, but are not limited to, antibodies such as anti-thymocyte globulin, anti-thymocyte globulin, and PF-06823859; antisense oligonucleotides such as alicaforsen sodium, ATL-1102, and QPI-1002; aptamers such as emapticap pegol and olaptesed pegol; bispecific monoclonal antibodies such as MaaT-013; blood derivatives such as SAR-156597 and albumin; fusion proteins such as alpha-1 proteinase inhibitor, etanercept, abatacept, rilonacept, belatacept, alefacept, SL-401, atacicept, RCT-18, CD-24Fc, F-652, RSLV-132, MDNA-55, and T-Guard; monoclonal antibodies such as adalimumab, infliximab, ustekinumab, eculizumab, golimumab, natalizumab, tocilizumab, certolizumab pegol, vedolizumab, secukinumab, lemtrada, belimumab, canakinumab, obinutuzumab, ixekizumab, daclizumab, alemtuzumab, ocrelizumab, tildrakizumab, siltuximab, brodalumab, basiliximab, ABCream, reslizumab, muromonab-CD3, dupilumab, efalizumab, sarilumab, guselkumab, risankizumab, emapalumab, ravulizumab, xilonix, OMS-721, BI-655130, mirikizumab, ozoralizumab, leronlimab, ianalumab, bimekizumab, infliximab biobetter, ocaratuzumab, tralokinumab, inolimomab, olokizumab, anifrolumab, belimumab+rituximab, BCD-085, basiliximab biobetter, BIVV-009, RG-6107, IFX-1, talacotuzumab, namilumab, otelixizumab, bleselumab, BT-063, foralumab, SAL-021, monoclonal antibody to antagonize IL-2R beta for celiac disease, oncology and tropical spastic paraparesis, vobarilizumab, brazikumab, KHK-4083, GBR- 830, CNTO-6785, clazakizumab, lebrikizumab, (dectrekumab+VAK-694), orilanolimab, RPC-4046, REGN-3500, iscalimab, prezalumab, sirukumab, BOS-161721, BCD-089, dapirolizumab pegol, AMG-714, siplizumab, BIIB-059, monoclonal antibody to inhibit TNF-alpha for musculoskeletal disorders, MOR-106, OPN-305, BMS-986253, GSK-2330811, rozanolixizumab, CJM-112, KPL-301, etokimab, and ANB-019; oligonucleotides such as defibrotide sodium; polysaccharides such as dociparstat sodium; proteins such as C1 esterase inhibitor, bee venom, ARG-201, and PRTX-100; recombinant enzymes such as imlifidase; recombinant proteins such as anakinra, C1 esterase inhibitor (recombinant), tadekinig alfa, nomacopan, sanguinate, dekavil, ABY-035, INV-103, and tiprelestat; small molecules such as lenalidomide, fingolimod hydrochloride, tacrolimus, sildenafil citrate, teriflunomide, pomalidomide, apremilast, tofacitinib citrate, pirfenidone, ambrisentan, mycophenolate mofetil, bendamustine hydrochloride, cyclosporine, zortress, mycophenolate sodium DR, sirolimus, thalidomide, mizoribine, tranilast, methotrexate, hydrocortisone, panobinostat, maxtrex, leflunomide, tofacitinib citrate ER, icosapent ethyl, cladribine, baricitinib, gusperimus trihydrochloride, amifampridine phosphate, sonidegib phosphate, tacrolimus ER, mizoribine ODT, lefluonomide, methoxsalen, azathioprine, rofecoxib, avacopan, glasdegib, peficitinib hydrobromide, ozanimod hydrochloride, AC-203, brimonidine tartrate, reproxalap, voclosporin, BMS-986165, abrocitinib, delgocitinib, ponesimod, cenicriviroc, seletalisib, reparixin, BB-3, leniolisib, epinephrine, ACT-774312, didox, LC-280126, VB-201, IBsolvMIR, cyclosporine CR, PF-06650833 MR, lipidated tacrolimus, KZR-616, AS-101, CC-11050, JTE-051, entospletinib, cannabidiol, PRN-1008, grapiprant, hydroxytriptolide, PF-06700841, PF-06651600, laquinimod sodium, sotrastaurin acetate, KD-025, emricasan, RGI-2001, diacerein, spebrutinib besylate, cerdulatinib, ubidecarenone, NC-2400, AKP-11, arsenic trioxide, poseltinib, GKT-831, levalbuterol sulfate, ladarixin, cenerimod, iberdomide hydrochloride, diacerein CR, GS-9876, RG-7625, evobrutinib, YRA-1909, and forigerimod acetate; synthetic peptides such as APL-2, ampion, RGN-259, brimapitide, cibinetide, CBLB-612, BNZ-1, and RA-101495; MT-7117; ICP-022, and Myadept.

FIGS. 1A-1B show an exemplary embodiment of the reservoir chamber 140.

The reservoir chamber can be considered to have a height or thickness determined by a dimension that extends vertically from the support structure (that separates the cell chamber and reservoir chamber) to a surface distal to the support structure. The size of the reservoir chamber can be varied depending on the contents of the reservoir, the volume of the reservoir, the intended use, and the like. In some embodiments, the reservoir can hold a volume of from 10 μL to 200 μL, for example, from 10 μL to 175 μL, from 10 μL to 150 μL, from 10 μL to 125 μL, from 10 μL to 100 μL, from 10 μL to 75 μL, from 10 μL to 50 μL, from 10 μL to 25 μL, from 25 μL to 200 μL, from 25 μL to 175 μL, from 25 μL to 150 μL, from 25 μL to 125 μL, from 25 μL to 100 μL, from 25 μL to 75 μL, from 25 μL to 50 μL, from 50 μL to 200 μL, from 50 μL to 175 μL, from 50 μL to 150 μL, from 50 μL to 125 μL, from 50 μL to 100 μL, from 50 μL to 75 μL, from 75 μL to 200 μL, from 75 μL to 175 μL, from 75 μL to 150 μL, from 75 μL to 125 μL, from 75 μL to 100 μL, from 100 μL to 200 μL, from 100 μL to 175 μL, from 100 μL to 150 μL, from 100 μL to 125 μL, from 125 μL to 200 μL, from 125 μL to 175 μL, from 125 μL to 150 μL, from 150 μL to 200 μL, from 150 μL to 175 μL, or from 175 μL to 200 μL. In some embodiments, the reservoir can contain a payload with a dosage designed for a specific purpose. Useful dosages of the compounds and agents and pharmaceutical compositions useful with the devices disclosed herein can be determined by those skilled in the art, for example, by comparing their in vitro activity, and in vivo activity in animal models. Methods for the extrapolation of effective dosages in mice, and other animals, to humans are known to the art; for example, see U.S. Pat. No. 4,938,949.

The thickness of the reservoir chamber can also be varied depending on the contents of the reservoir, the volume of the reservoir chamber, the intended use, and the like. In some embodiments, the thickness of the reservoir chamber can be less than 5 mm, e.g., 4.5 mm or less, 4 mm or less, 3.5 mm or less, or 3 mm or less. In other examples, the thickness of the reservoir chamber can be 2 mm or greater, e.g., 2.5 mm or greater, 3 mm or greater, or 3.5 mm or greater. In certain embodiments, the thickness of the reservoir chamber can be from 2.5 mm to 5 mm, from 3 mm to 5 mm, or from 2.5 mm to 4.5 mm.

The reservoir chamber can also comprise one or more loading ports (also referred to herein as second openings, injection ports, or drug loading and venting port 141) for drug loading. In some examples, the loading port can be accessed through the skin of the host. The reservoir chamber is not vascularized and is free from tissue. In some embodiments, the loading port can be made of materials that is penetrable with a medical needle and resealable after the penetration. Such materials include plastic, rubber, or silicone. The payload can be filled into the reservoir chamber through the loading port and then sealed. In some embodiments, the size of the loading port can be from 0.5 mm to 3 mm, from 0.5 mm to 2 mm, or from 1 mm to 2 mm Support Structure The devices disclosed herein include a support structure separating the cell chamber and reservoir chamber. The support structure need not provide structure support for the entire device or the housing (though it can); it need only provide support for the membrane between the reservoir and cell chambers. FIGS. 1A and 1B show an exemplary device comprising a support structure 120. The support structure is bound by the perimeter wall of the housing and extend laterally along a horizontal axis running from a first side to a second side of the housing. In some embodiments, the support structure can extend along the long axis running from a first side to a second side of the housing.

The support structure, with the membrane, can be defined by its surface area. In some embodiments, the surface area of the support structure can be at least 50 $mm^2$, at least 55 $mm^2$, at least 60 $mm^2$, at least 65 $mm^2$, at least 70 $mm^2$, at least 75 $mm^2$, at least 80 $mm^2$, at least 85 $mm^2$, at least 90 $mm^2$, at least 95 $mm^2$, at least 100 $mm^2$, at least 110 $mm^2$, at least 120 $mm^2$, at least 140 $mm^2$, at least 150 $mm^2$, at least 175 $mm^2$, at least 200 $mm^2$, at least 250 $mm^2$, at least 300 $mm^2$, or at least 350 $mm^2$. In some embodiments, the surface area of the support structure can be 500 $mm^2$ or less, 450 $mm^2$ or less, 400 $mm^2$ or less, 350 $mm^2$ or less, 320 $mm^2$ or less, 300 $mm^2$ or less, 250 $mm^2$ or less, 200 $mm^2$ or less, 175 $mm^2$ or less, 150 $mm^2$ or less, 125 $mm^2$ or less, or 100 $mm^2$ or less. In some embodiments, the surface area of the support structure can be from 50 $mm^2$ to 500 $mm^2$, from 75 $mm^2$ to 500 $mm^2$, from 100 $mm^2$ to 500 $mm^2$, from 110 $mm^2$ to 500 $mm^2$, or from 100 $mm^2$ to 350 $mm^2$.

The support structure 140 can comprise a membrane. The membrane is of a "semi-permeable" nature to permit drugs, particles, and/or biomolecules for example to diffuse from the drug reservoir into the cell chamber. Numerous variables can affect the pharmacokinetics of drugs, particles, and/or biomolecules release. The membrane of the preferred embodiments can be optimized for short- or long-term release. In membrane of the preferred embodiments can be optimized to provide short-term release of drugs, particles, and/or biomolecules from the reservoir chamber to the cell chamber. In membrane of the preferred embodiments can be optimized to provide long-term release of drugs, particles, and/or biomolecules from the reservoir chamber to the cell chamber. In membrane of the preferred embodiments can combine short-term and long-term release of drugs, particles, and/or biomolecules from the reservoir chamber to the cell chamber. As used herein, "controlled," "sustained," or "extended" release of the factors can be continuous or discontinuous, linear or non-linear.

In some embodiments, the membrane can be a nano-channel membrane. Nano-channel membranes are described in PCT/US2016/032658 filed May 16, 2016, which is incorporated herein by reference in its entirety. Briefly, the nano-channel membrane can include hundreds of thousands of densely packed nano-channels with precisely controlled size and surface properties. At the nanoscale, molecular interactions with the channel wall dominate the transport of fluids to such an extent that the classical mechanical laws of diffusion (Fick's laws) break down. Thus, nanoscale phenomena are used herein to achieve the goal of constant release of nanoparticles and bioactive agents over periods of time ranging from weeks to months and over a broad range of molecular sizes, at release rates relevant for medical applications. Constant and sustained release can be achieved with a large number of molecules ranging from small molecular weight (MW) peptides, and common immunosuppressant drugs, as well as large MW. The experimental analysis has been focused on the release of drug from solutions stored in a source reservoir. In some embodiments, the nano-channel membrane can offer tightly-controlled release of drugs, particles, and/or biomolecules through its high spatial and electrostatic hindrance channels.

The nano-channels can be fabricated with varying height and channel density, enabling tuning to fit a given molecule and desired dose release rate. For example, the nano-channel membranes can have nano-channels from 2.5 nm to 1000 nm in diameter, for example, from 2.5 nm to 750 nm, from 2.5 nm to 500 nm, from 2.5 nm to 100 nm, from 2.5 nm to 75 nm, from 2.5 nm to 50 nm, from 2.5 to 25 nm, from 5 nm to 75 nm, from 5 nm to 50 nm, from 5 nm to 25 nm, from 10 nm to 75 nm, from 10 nm to 50 nm, from 10 nm to 25 nm, from 20 nm to 75 nm, from 20 nm to 50 nm, from 40 nm to 100 nm, from 40 nm to 75 nm, from 50 nm to 100 nm, from 50 nm to 75 nm, from or from 75 nm to 100 nm, from 100 nm to 1000 nm, from 500 nm to 1000 nm, or from 750 nm to 1000 nm. The density of the nano-channels in the membrane can be at least 50,000, at least 100,000, or at least 150,000 nano-channels $mm^2$.

In general, it is desirable that the drug diffusion across the membrane is homogenously and locally distributed to the cell chamber. To optimize local delivery of the drug to the cell chamber, the membrane can be micro-fabricated with photolithographic techniques from a silicon material or polymer material, allowing for fine control over channel size and distribution in the 20-1000 nm range. In some embodiments, the membrane can provide local release of a bioactive agent for example, within a distance of 5 mm or less, e.g., 4.5 mm or less, 4.0 mm or less, or 3.5 mm or less. In the disclosed device, the membrane can locally deliver a drug from the drug reservoir to the cells in the cell chamber, protecting them from the immune system and enhancing their vascularization.

To improve the homogeneity of the drug delivery to the cells in the cell chamber, there is a need to optimize the volume of the drug being delivered to the effective area of the cell chamber. The effective area of the cell chamber is a two dimensional area in the x and y dimension that is occupied by the cells in the cell chamber. To optimize the volume of drug being delivered to the effective surface area, the surface are of the membrane (which allows for fluid communication between the drug reservoir and cell chamber) can be optimized.

In some embodiments, the membrane can define a surface area that is at least 50% of a total surface area of the support structure (separating the drug reservoir and cell chamber). For example, the membrane can define a surface area that is at least 55%, at least 60%, at least 65%, at least 70%, at least 75%, at least 80%, at least 85%, at least 90%, at least 95%, at least 98%, at least 59%, or up to 100% of a total surface area of the support structure. In some embodiments, the membrane forms the entire support structure separating the cell chamber and the reservoir chamber.

The membrane can be made of silicon-containing materials or it can be a polymer like polyester, polycarbonate, poly(meth)methacrylate, or polylactic acid.

Methods of Making

Methods for making the devices described herein are also disclosed. In certain embodiments, the device can be fabricated using a custom 3D printer technology. In some embodiments, the 3D printer can run on a fused deposition modeling (FDM) technique, building parts layer-by-layer from the bottom-up by heating and extruding thermoplastic filament. The 3D printer alternatively can run on or stereolithography (SLA) technique, building layers by focusing light onto a photopolymer. A solid modeling software (SolidWorks™, Dassault Systèmes SolidWorks Corp.) can be used to create a 3D dataset for the fabrication process. In some instances, the housing can be fabricated using a custom 3D printer technology while the membrane can be fabricated as described in PCT/US2016/032658 filed May 16, 2016 (for example, through removal of atomic layer deposited tungsten (a sacrificial layer) by $H_2O_2$ etching).

After fabrication, the device can be surface modified as described herein to, increase its hydrophilicity and to obtain a suitable external charge for example. In specific examples, the surface of the device can be plasma treated. Plasma treatment can include immersing the device in a base such as 5 M NaOH followed by rinsing and drying. An argon plasma (Ar) or oxygen plasma ($O_2$) etching process can be carried out. Other methods of surface modification include attaching an endothelial cell attachment factor.

Methods of Using

Methods for using the devices are also disclosed herein. The devices can be used for delivering cells into a human or non-human subject. The cell delivering method can be a multistep process comprising a device implantation step followed by a cell and optionally drug infusion step. In some embodiments, the method can include implanting a device as disclosed herein in the subject's body prior to delivery of the cells. The implanted device can be maintained in the host for an adequate time for collagen and blood vessels to infiltrate the micro-channels of the cell chamber. In some embodiments, device can be sterilized using ethylene oxide, gamma radiation or dry heat autoclaving, for example, prior to implantation. The type of sterilization method used is dependent on the housing material, since dry heat autoclaving may warp certain polymeric materials (e.g. polypropylene) due to low heat deflection temperature.

The device can be implanted subcutaneously, percutaneously, transcutaneously or intraperitoneally. For example, for subcutaneous implantation of the device in the subject, an incision can be made through the dermis and epidermis followed by careful blunt dissection of connective tissue and adipose, creating a subcutaneous pocket caudal to the incision line. Once an adequate space is created (roughly the dimensions of the device), the device can be implanted into the subcutaneous pocket, and the incision is sutured. Alternatively, the device can be implanted in the peritoneal cavity through an abdominal incision. The device implantation steps can be followed by a device incubation period during which a vascularized matrix is deposited in and around the cell chamber.

After the incubation period, cells can be loaded transcutaneously through the port, without surgery when the device is implanted subcutaneously. If the device is implanted in certain deeper sites, access can be obtained via a second surgery (e.g., laparoscopic surgery). Delivery of a cellular preparation into the device can be made by using a cell delivery apparatus. The delivery apparatus (such as a syringe or cell infusion tube) can be loaded with the cellular preparation, and the syringe or tube can be inserted into the injection port of the cell chamber. When the device is completely filled with the cellular preparation, cell infusion can be stopped and the delivery device retracted from the device.

Prior to, during, or after delivery of the cellular preparation, the method can further include delivery of a drug preparation into the reservoir chamber. For administering the drug preparation into the device, a delivery apparatus (such as a syringe) can be loaded with a drug preparation, and the apparatus can be inserted into the injection port of the reservoir chamber. When the device is completely filled with the drug preparation, drug infusion can be stopped and the delivery apparatus retracted from the device. The injection port can be closed or can close automatically. In some embodiments, the drug preparation can be delivered into the device prior to implantation of the device.

The devices and methods disclosed herein can be used for transplantation of any therapeutic cells, or a combination of cells, into a host body for providing therapeutic biological material to the host for the treatment of a disease condition. The cells may be allogeneic, xenogeneic or syngeneic donor cells, patient derived cells, including stem cells, cord blood cells and embryonic stem cells. The stem cells may be differentiated into the appropriate therapeutic cells. The cells may be immature or partially differentiated or fully differentiated and mature cells when placed into the device. The cells may also be genetically engineered cells or cell lines.

In some aspects of the device, the device can be used for transplantation of insulin producing cell aggregates (ILIPAs), Leydig cells, pancreatic islets cells, or a combination thereof. In some aspects of the device, the device can be used for transplantation of islets of Langerhans cells to assist blood glucose regulation in the host body. In other aspects, the device can be used for co-transplantation of islets of Langerhans and Sertoli cells, where the Sertoli cells provide immunological protection to the islet cells in the host body. The immune protection provided by Sertoli cells in a host body was previously disclosed, for example, in U.S. Pat. No. 5,725,854, which is incorporated herein by reference in its entirety. In other aspects, the device can be used for co-transplantation of mesenchymal stem cells, where the cells provide immunological protection to the islet cells in the host body. Also disclosed are methods of treating various diseases by transplanting therapeutic amounts of cells to subjects in need thereof using the device as disclosed here.

In further aspects, the device can be used for transplantation of cells that release hormones. In still further aspects, the device can be used for transplantation of human embryonic stem cells (hESCs) and pluripotent stem cells (iPSCs) differentiated to obtain insulin producing cells, adult somatic cells, hepatocytes, fibroblasts, kidney cells (e.g., genetically engineered to secrete human ciliary neurotrophic factor).

The density of the transplanted therapeutic cells, or combinations of cells, can be determined based on the body weight of the host and the therapeutic effects of the cells. As noted earlier, the dimensions of the cell chamber and number of micro-reservoirs to be used (in a device) are determined based on the number of the cells required, the extent of vascularization achievable during the device incubation period, and the diffusion characteristics of nutrients and cellular products in and out of the implanted devices.

EXAMPLES

The devices, methods and compositions of the appended claims are not limited in scope by the specific methods and compositions described herein, which are intended as illustrations of a few aspects of the claims and any methods and compositions that are functionally equivalent are within the scope of this disclosure. Various modifications of the methods and compositions in addition to those shown and described herein are intended to fall within the scope of the appended claims. Further, while only certain representative methods, compositions, and aspects of these methods and compositions are specifically described, other methods and compositions and combinations of various features of the methods and compositions are intended to fall within the scope of the appended claims, even if not specifically recited. Thus, a combination of steps, elements, components, or constituents can be explicitly mentioned herein; however, all other combinations of steps, elements, components, and constituents are included, even though not explicitly stated.

Example 1: 3D Printed Vascularized Device (Cell Chamber) for Subcutaneous Transplantation of Human Islets Discoidal encapsulation devices (8 mm in diameter and 2.5 mm in thickness, FIG. 2A) suitable for holding up to 5,000 islets were printed adopting a Fused Deposition Method (FDM) based 3D printer (REPLICATOR™ 2×, MakerBot Industries) and medical grade polylactic acid (PLA, Foster Corporation). The two inner surfaces were composed of an array of micro-reservoirs (300 µm×300 µm) to house the transplanted islets individually, maintaining them in close proximity while avoiding clustering. These micro-reservoirs are connected to surrounding tissues by an array of square micro-channels (100 µm×100 µm cross section, 50 µm length) to allow for the growth of transmembrane blood vessels in view of graft vascularization. The devices featured a loading port (1 mm diameter) for transcutaneous cell loading. Device surfaces were treated with argon and oxygen plasma (March plasma etcher, Nordson). The power (30 W) and gas flow (150 mTorr) were kept constant, while changing the exposure time (30, 90, 120 and 150 seconds). The nano-pattering of the device surfaces was evaluated before and after treatment by scanning electron microscopy (SEM) (Nova NanoSEM, FEI) for channel quality and size. Hydrophilicity was evaluated by measuring the water contact angle and surface roughness was evaluated by atomic-force microscopy set in tapping mode (BioScope Catalyst, Bruker Instruments, Texas).

The encapsulation systems were evaluated in nude mice (Nu/Nu, female, 8-10 week old), after receiving approval by the Institutional Animal Care and Use Committee of Houston Methodist Research Institute. Surface treated and sterilized devices, loaded with platelet-lysate matrix (PLM) enriched with VEGF at two different concentrations (0.5 and 5 µg/mL), were implanted subcutaneously in the mice dorsum (n=12 per group). At 1, 2, and 4 weeks post implantation, 4 mice per group were euthanized and the graft explanted for the histological assessment of vascularization and innervation. The implant and surrounding tissues were harvested and processed for histopathology evaluation of tissue response to the implanted device. CD31 antibody (Abcam, ab28364) and a pan-axonal antibody (Cambridge Bioscience, SMI-312R-100) were used to assess vascularization and innervation, respectively. A second experiment was performed in nude mice (n=5 per group) to evaluate insulin release from human islets transplanted into a pre-vascularized device. Human pancreatic islets (2,000 IEQ per mice) were injected with a 22 G needle transcutaneously into the encapsulation system 4 weeks after device implantation. Islets implanted under the kidney capsule served as positive control. 10 Human insulin (ultra-sensitive human insulin ELISA kit, Alpco) and blood glucose (OneTouch® Glucometer, Johnson and Johnson) levels were assessed weekly and body weight was monitored throughout the experiment. Intra peritoneal glucose tolerance test (IPGTT) was performed weekly to assess insulin secretion, in response to stimuli, from the transplanted islets. A subsequent test was performed on the same animal cohort to demonstrate the refillability of the implant. Twelve weeks after the first injection, additional human islets (2,000 IEQ per mice) were injected transcutaneously in all groups where the insulin production was lower than 0.125 µIU/mL.

All data are represented as average and standard error of the mean (SEM) and statistical analysis performed using Student's paired t-test. A value of $p<0.05$ was considered statistically significant. GraphPad Software, Inc. was used for the analysis.

Results & Discussion: Transplantation of islets on porous biomaterials has emerged as a promising strategy for long-term islet function facilitating rapid tissue ingrowth, vascularization and innervation providing oxygen, nutrition, and waste removal. Recognizing such needs for an islet and cell encapsulation system, a new strategy to deliver cells subcutaneously is exemplified. The architecture of the device is designed to maintain pancreatic islets close to blood vessels in a growth factor enriched environment, but separated from each other to mimic the physiological architecture in the pancreas and avoid cell crowding.

Figures 2A, 2B, 2C, 2D, 2E:
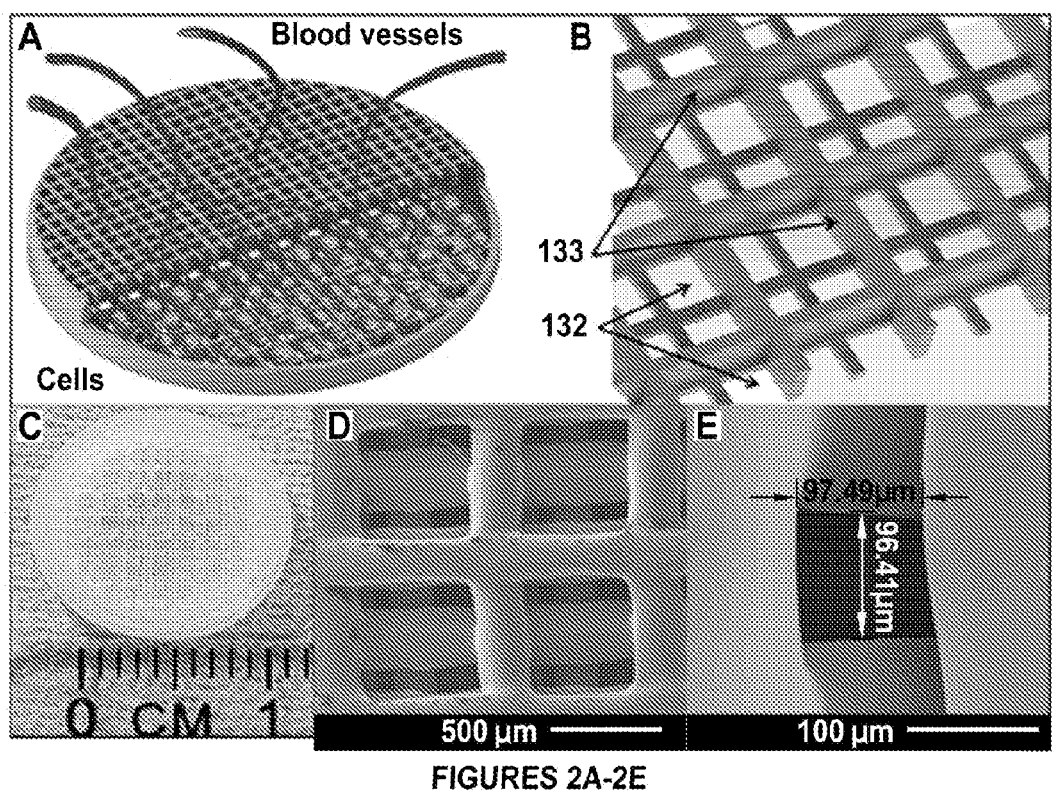
FIGS. 2A-2E are images showing a cell chamber of the cell transplantation device.
Figure 3:
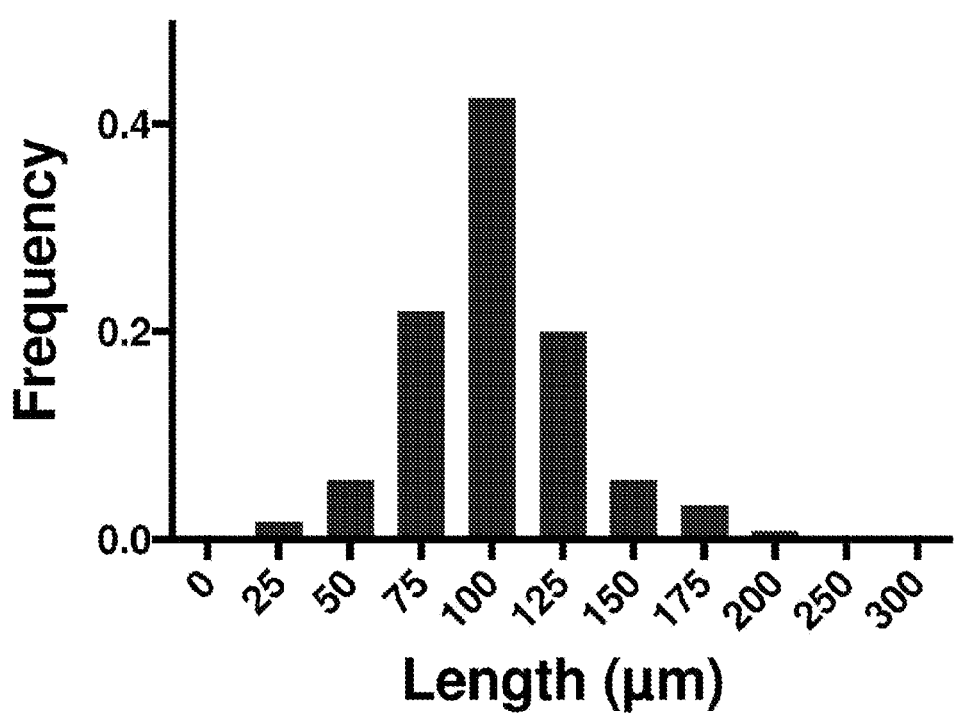
FIG. 3 is a bar graph showing the size distribution of the micro-channels in the cell chamber.

To increase the bio-integration of the encapsulation system, PLA, which is a widely adopted polymer in biomedical devices, biocompatible, and presents good elasticity and mechanical strength suitable for subcutaneous implantation was used. Due to the chiral nature of lactic acid, PLA is hydrophobic and may exhibit low cell adhesion properties. Surface treatment with plasma improves the low surface free energy of different materials and offers a solvent-free technique capable of changing the wettability, surface roughness and surface chemistry of polymers, enhancing cell proliferation and viability. Plasma activation also increases PLA's surface free energy forming a broad variety of functional groups on the surface, including polar groups, which drastically change wettability and have a positive effect on material-cell interactions. Previous work has demonstrated that plasma treatment substantially increased the hydrophilicity of the surface and reduced the contact angle, which remained stable over 30 days in phosphate buffered saline (PBS). Here the effect of plasma exposure time on surface patterning and roughness was investigated and compared oxygen and argon treatments. As shown in FIG. 2D, both treatments increased surface roughness, reaching a maximum value, after which the roughness diminished with continued exposure, possibly due to eventual etching of the crystalline regions. It was also noticed that the oxygen treatment caused deeper patterns (4.63 nm with argon and 26.45 nm with oxygen, $p<0.01$, FIG. 2E), which has been demonstrated to be beneficial for cell attachment and proliferation.

Figures 5A, 5Q:
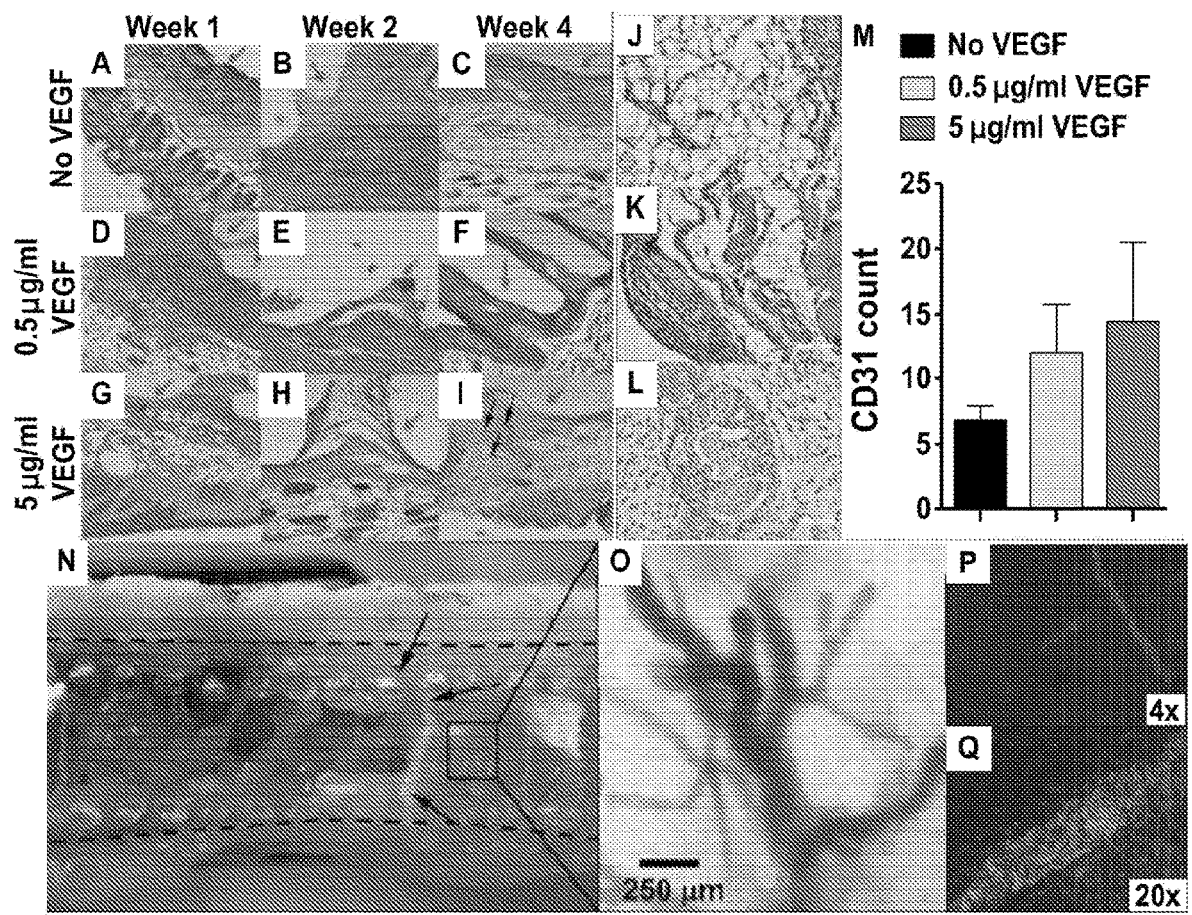
FIGS. 5A-5Q shows hematoxylin and eosin staining of the tissue surrounding the device at 4x.
Figures 6A, 6B, 6C:
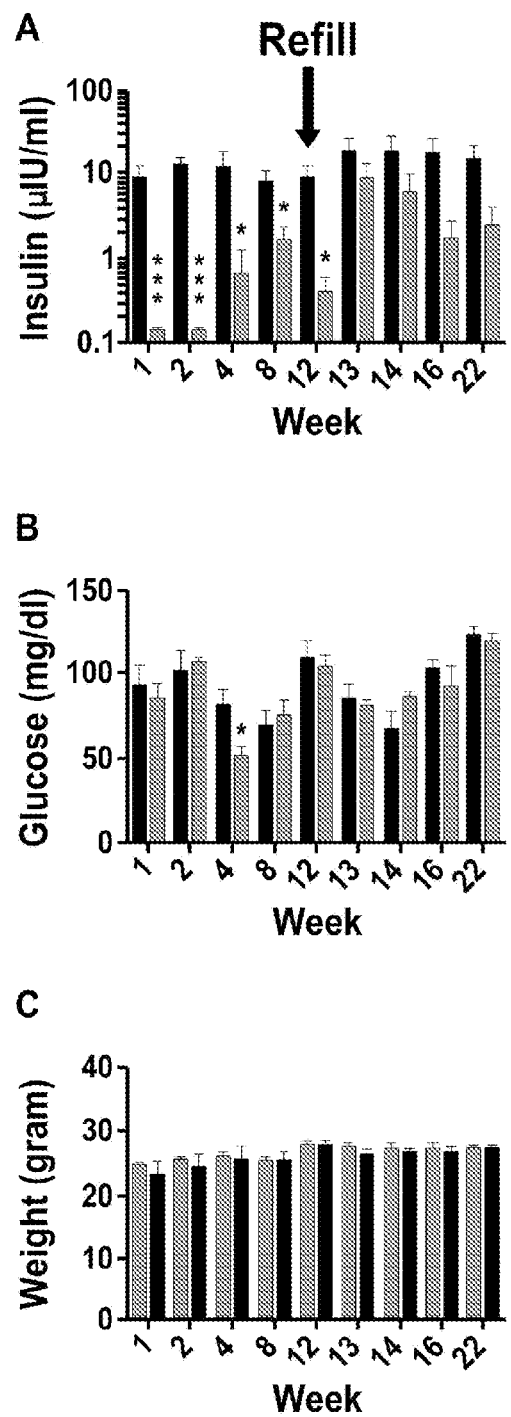
FIGS. 6A-6C show insulin release from kidney capsule (black) and the device (red) after glucose stimulation (FIG. 6A). On week 12, all the animal with insulin level below 0.125 uU/mL were treated by refilling the implant with additional 2000 IEQ (red arrow).

In vivo vascularization and innervation of oxygen treated devices after subcutaneous implantation in nude mice was then investigated. Nude mice show an inflammatory response to a foreign body, but allow for transplantation with human islets without the need for immunosuppression. It has been broadly demonstrated that vascularization of the graft is the key for successful engraftment of islet transplants. Prevascularization could mitigate the issue of acute hypoxia which was shown to result in islet apoptosis and graft failure. To stimulate neovascularization and to support the islet viability and function for a period of time after transplantation, devices loaded with biological gels with different VEGF concentrations was used. An acute inflammatory response to the foreign body was present in the first week after device implantation, mainly in the VEGF groups, and subsided with time, leaving a rim of vascularized connective tissue around the device at week 4 (FIGS. 5A-5I). Indeed, the neutrophils, which are considered of impact for the development of the inflammatory response which leads to the formation of the fibrotic capsule, were almost absent from the second week (FIGS. 5A-5I). The red arrows in FIGS. 5A-5I indicate the protrusion of the surrounding subcutaneous tissue into the devices. Tissue samples were taken from the side of the device closer to the skin, representing the subcutaneous environment. A positive trend between VEGF concentration and the number of vessels stained by CD31 (FIGS. 5J-5M) was noted. However, after 4 weeks, calcification in the VEGF 5 µg/mL sample (FIG. 5I) as evident by the dark spots in high density close to the tissue-implant interface was observed. It was also observed that in 4 weeks the subcutaneous tissue and the inside of the device were vascularized (FIGS. 5N-5O). Based on these results, 0.5 µg/mL VEGF was selected for further studies. Finally, nerve bundles in the proximity of the device (FIGS. 5P-5Q) were found, indicating their potential to reach the transplanted islets.

After vascularization, a second experiment was conducted injecting human islet into a pre-vascularized device. Detectable levels of human insulin from week 4, but at lower levels compared to the positive control ($p<0.001$) was observed. As described in various islet encapsulation models, there is a lag time for adequate function until the transplanted islets are vascularized. The pre-vascularization of the device appeared to have helped encapsulated islets to overcome the initial post implant injury, but it takes a few weeks for the transplanted cells to develop mature vasculature and be functional.

A second load of islets (2,000 IEQ) into vascularized devices increased the insulin levels (~10 µIU/mL) to values that were comparable to the kidney capsule transplantation ($p>0.05$). Additionally, the devices were well tolerated and animals showed comparable basal glucose level and weight, demonstrating that the presence of additional islets is not associated with hypoglycemia.

Summary: In this example, it was shown that the subcutaneous implantation of a 3D printed and functionalized cell encapsulation system generates adequate and prompt vascularization of the graft. Vascularization was enhanced by the ability to dispense pro-angiogenic factors, such as VEGF, which is also known to increase islet viability and function. In addition, the device could protect the graft, while the islets are being vascularized, from initial transplant site stressors and support their long-term survival. The transcutaneous refillability of the device offers opportunities for cell supplementation, without surgical retrieval and re-implantation, to accommodate changing physiological needs. This will be of significant advantage in the case of the growing children with diabetes. Moreover, the reservoir structure permits the potential retrievability of the graft, which is important for stem cell derived engineered cells, undergoing malignant or other unwanted transformations. Though the current studies were done in immunodeficient animal models, the device can be incorporated with local delivery of immunomodulators, which will expand its evaluation in immunocompetent diabetic animals. Further studies in diabetic animal models are required to prove the efficacy of this versatile encapsulation system for diabetes cell therapy.

Example 2: Implantable Capsule (Drug Reservoir) Assembly

Nano-channels membranes were fabricated through industrial silicon manipulation processes initially developed within the microelectronics industry. The specifics of the disclosed process to produce nano-channel membranes have been described previously (e.g., A. Grattoni, et al., *Anal Chem.* 83, 3096-103 (2011)). Briefly, nano-channels with a height of 20 nm were generated within the silicon membranes through removal of atomic layer deposited tungsten (a sacrificial layer) by $H_2O_2$ etching. The resulting slit-nano-channels were characterized as having a defined and repeatable architecture. Individual channels were parallel to the membrane surface and perpendicular to micro-channels running to either membrane surface. This configuration was adopted to promote high nano-channel density and physical robustness, as the membranes could withstand differential pressures in excess of 4 MPa (D. Fine, A. et al., *Adv Healthcare Mater.* 2, 632-666 (2013)). Following the sacrificial etching process, isopropyl alcohol was substituted for water prior to drying to minimize surface tension.

Once fabricated, nano-fluidic membranes with 20 nm nano-channels on 6.0×6.0×0.70 mm silicon chips were subdivided with an ADT 7100 precision dicing saw (Advanced Dicing Technologies, Ltd., Yokneam, Israel) into squares approximately 0.75×0.75×0.70 $mm^3$. Scanning electron microscopy (SEM) images of the membranes before and after sectioning are shown in FIGS. 4A and 4B. The diced chips were piranha washed in 70% $S_2O_4$ and 30% $H_2O_2$, inserted within the end of 3 mm tubes made of either 18G 316 stainless steel (McMaster-Carr, Atlanta, Ga.) or PEEK (IDEX Health and Science, Oak Harbor, Wash.), and epoxied into place. The tubes acted as system casings and drug reservoirs. The various tubing materials were selected to be complementary with different imaging modalities. Stainless steel capsules offered high X-ray computed tomography (CT) contrast, while the PEEK capsules were compatible with magnetic resonance imaging (MRI) and utilized in this study for the release and detection of Magnevist (Bayer, Leverkusen, Germany) The second end of each tube was sealed with silicon adhesive (Nusil, Carpinteria, Calif.) to provide a resealable access point for drug loading. Images of assembled nano-channel implants are shown in FIGS. 2A-2D. As the implants were approximately 3.5 mm long with a silicone cap at one end and a semi-hollow membrane set at the other, they presented a reservoir capacity of 2.5-3 μl. Drugs were loaded manually through the silicon caps with a 32G syringe needle. A second needle was inserted into the interior reservoir space through the silicone cap to allow venting during filling. Nano-channel capsules were weighed before and after the loading process to ensure proper dosage.

The drug eluting fiducial markers were loaded with a number of different molecules to examine release kinetics into simulated physiological solution in vitro. In a series of experiments, the implants were loaded with ~2.5 μL of OX86, FGK45, or Magnevist, placed in a 70 μL cuvette, and immersed in PBS. The cuvettes were sealed with tight-fitting lids and kept in an incubator at 37° C. The PBS solution was sampled and replaced daily. The OX86 and FGK45 release was quantified by micro-BCA assay (Sigma-Aldrich). The Magnevist was quantified through MR scanning. (7T magnet, cut-down 96-well plate in a wrist coil). An additional experiment for quantifying IgG release was conducted similarly, but at room temperature and quantified via UV-Vis spectroscopy at 280 nm sampled every 10 minutes.

Intratumoral Magnevist Release

Figures 7A, 7B, 7C:
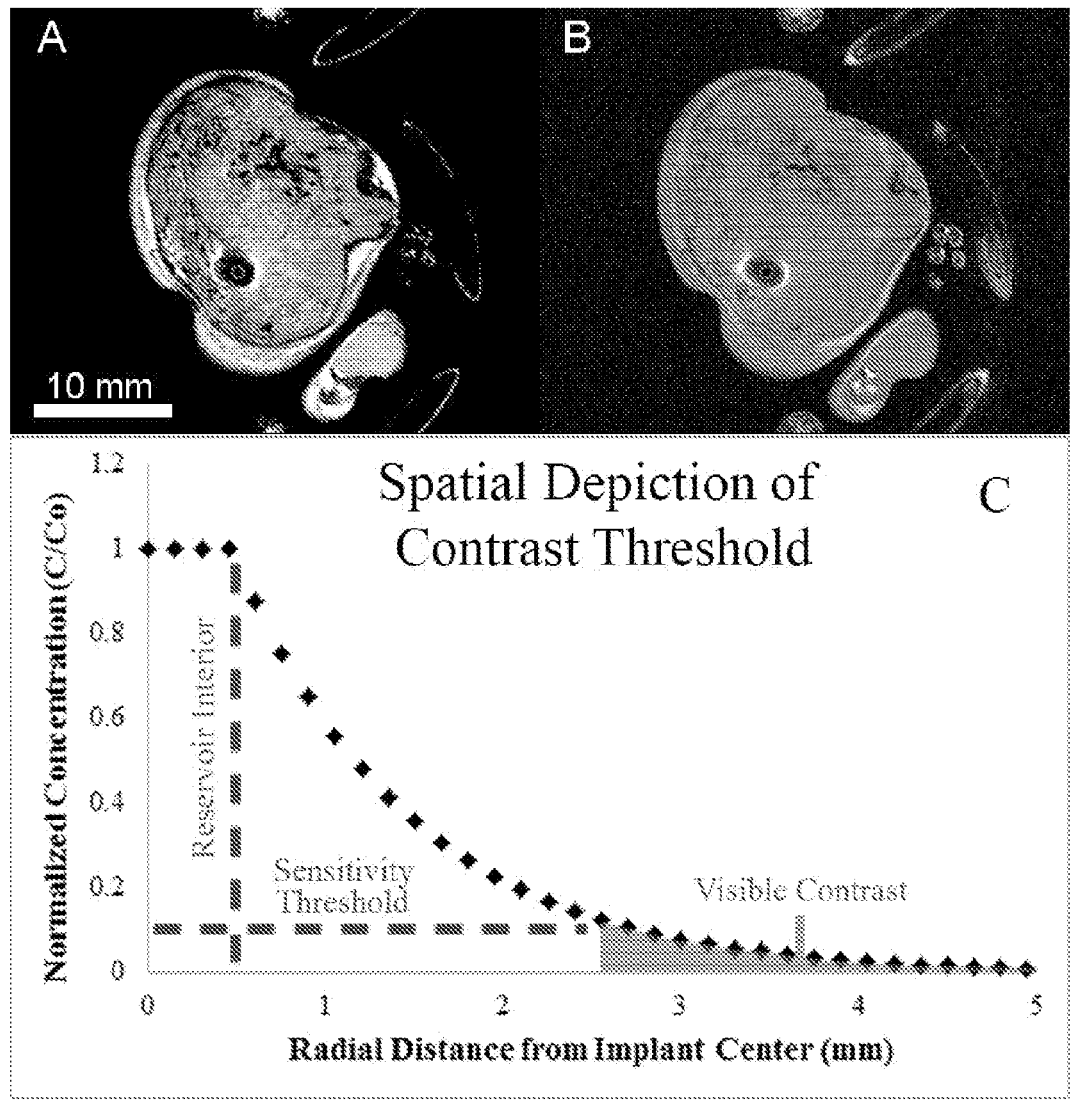
FIGS. 7A-7C are MR images from a representative mouse.
Figures 8A, 8B, 8C, 8D:
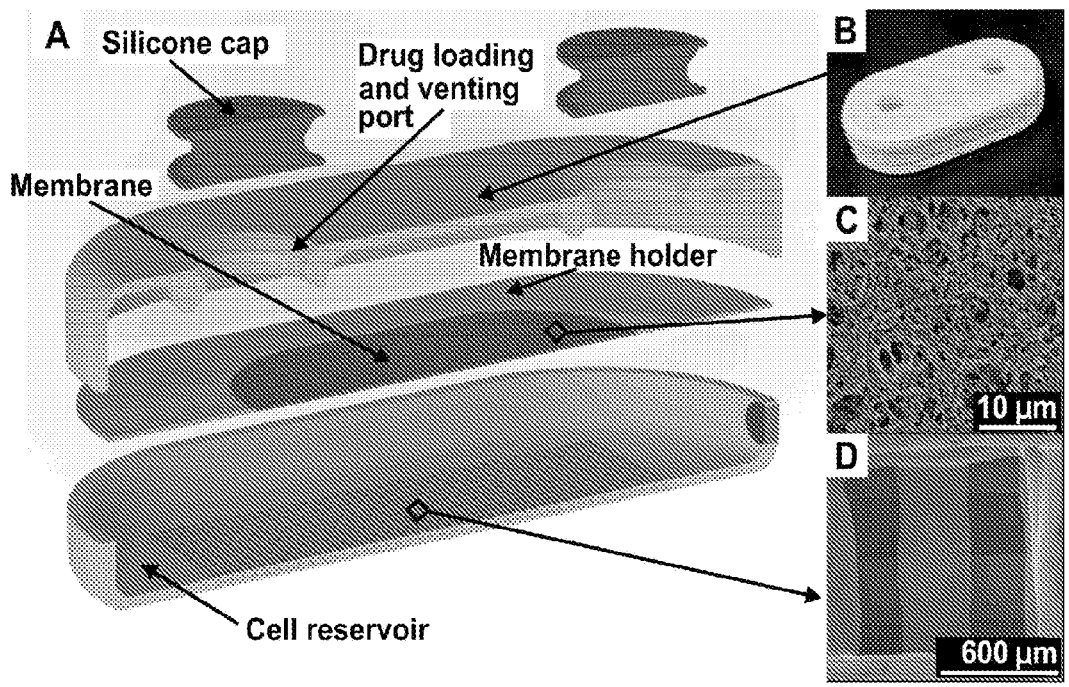
FIGS. 8A-8D are images showing a cross-section of exemplary cell transplantation device comprising a cell chamber and a drug reservoir chamber.
Figure 9:
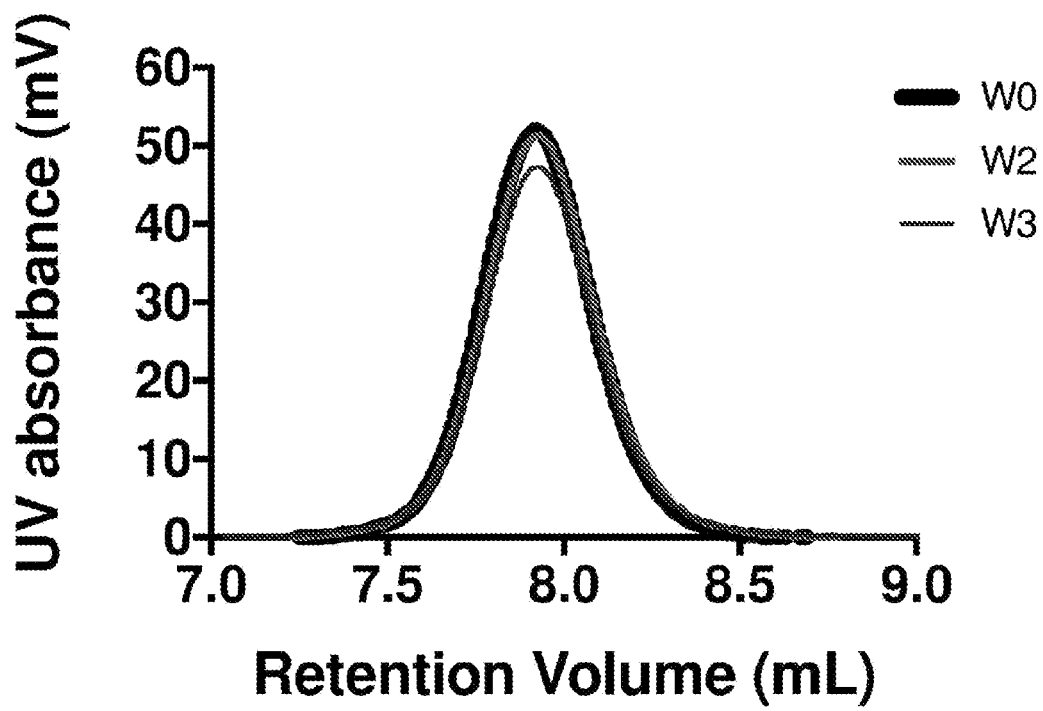
FIG. 9 is a graph showing CTLA4Ig stability at 37° C. The graph demonstrates that CTLA4Ig drug is stable for at least 3 weeks which supports the long term possibility to release this drug to protect the encapsulated cells.
Figure 10:
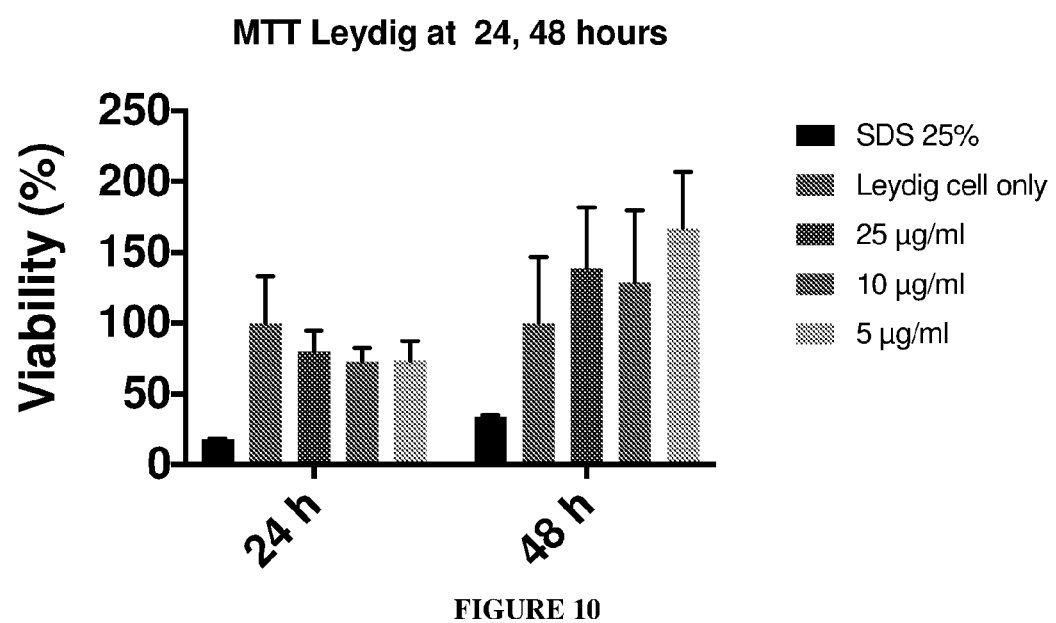
FIG. 10 is a bar graph showing viability and function of MTT Leydig cells over time. CTLA4Ig at different concentrations (5, 10, 25 µg/ml) does not affect viability and function of rat Leydig cells. Rat Leydig cells were cultured in media +CTLA4Ig followed by detecting the viability via MTT assay at 24 and 48 h.

Utilizing the percutaneous trocar delivery approach, PEEK nano-channel implants loaded with Magnevist were inserted intratumorally into the upper thigh of C57Bl6 mice with induced melanoma. T1- and T2-weighted images of the site 1 day after implantation are shown in FIGS. 7A-7C. The implants were visualized on T1-weighted images as an area of hypointensity corresponding to the PEEK body and surrounded by a hyperintense halo of contrast agent (FIG. 7B). Implant location could also be identified on T2-weighted images that, in addition, highlighted tumor heterogeneity (FIG. 7A). The average enhancing volume was found to be 75±25 $mm^3$ on day 1 and 65±13 $mm^3$ on day 3, implying substantial local clearance and similar release kinetics occurring as were observed for the Magnevist release in vitro.

PEEK implants demonstrated release over days. MR time-points were chosen based on the in vitro experiments, which exhibited rapid release for the first 2 days with substantial decrease on day 3. The lesser enhancement volume demonstrates that the Magnevist was cleared from the immediate tumor vicinity of the implant. An unexpected outcome was the implant's loaded concentration being too high for visualization, as the relaxation time was faster than the scanner could detect. This is further evidenced by the sharp onset of observable enhancement a few mm from the implant's exterior. The narrow band of this observable enhancement, beginning 2-5 mm from the implant's exterior and approximately 1 mm thick, provides evidence of rapid clearance of the contrast agent from the tumor tissue. FIG. 7C serves as an idealized graphical representation of the relationship between the normalized concentration and the visible contrast zone.

What is claimed is:
1. A device comprising:
a housing comprising a perimeter wall defining a cavity; and
a support structure separating the cavity into a cell chamber and a reservoir chamber, the support structure comprising a nano-channel membrane for fluid communication between the cell chamber and reservoir chamber, wherein the cell chamber defines a first opening comprising a microstructure; and wherein the nano-channel membrane defines a surface area that is at least 50% of a total surface area of the support structure, and wherein the microstructure in the cell chamber comprises:
  i. an array of micro-channels on an outer surface of the cell chamber, each micro-channel having a diameter to facilitate growth of vascular tissues; and
  ii. an array of micro-reservoirs on an inner surface of the cell chamber, each-reservoir having a diameter to facilitate housing of cell aggregates individually.

2. The device of claim 1, wherein the nano-channel membrane comprises nano-channels having a diameter from 2.5 nm to 1000 nm, and wherein the nano-channels are present at a density of greater than 100,000 nano-channels $mm^{-2}$ of the nano-channel membrane.

3. The device of claim 1, wherein the nano-channel membrane is derived from a silicon-containing material, or is chosen from polyester, polycarbonate, poly(meth)acrylate, or polylactic acid.

4. The device of claim 1, wherein each micro-channel has a diameter of from 10 μm to 200 μm, wherein each micro-reservoir has a diameter of from 50 μm to 500 μm, and wherein each micro-reservoir is in fluid communication with at least two micro-channels.

5. The device of claim 1, wherein the micro-reservoir comprises cell aggregates.

6. The device of claim 5, wherein the cell aggregates are insulin producing cell aggregates (ILIPAs), mesenchymal stem cells, Leydig cells, pancreatic islets cells, or a combination thereof.

7. The device of claim 1, wherein the reservoir chamber comprises one or more injection ports on an outer surface of the reservoir chamber.

8. The device of claim 1, wherein the reservoir chamber comprises a bioactive agent.

9. The device of claim 8, wherein the bioactive agent is an immunosuppressant drug or a growth factor.

10. The device of claim 8, wherein the nano-channel membrane provides controlled release of the bioactive agent.

11. The device of claim 1, wherein the housing of the device is derived from a biopolymer.

12. The device of claim 11, wherein the biopolymer is selected from polylactic acid (PLA).

13. A device comprising:
a housing comprising a perimeter wall defining a cavity; and
a support structure separating the cavity into a cell chamber and a reservoir chamber, the support structure comprising a nano-channel membrane for fluid communication between the cell chamber and the reservoir chamber, wherein the cell chamber defines a first opening comprising a microstructure, the nano-channel membrane defines a surface area that is at least 50% of a total surface area of the support structure, and an outer surface of the device is surface treated by coating with a biomaterial or by activating with plasma.

14. A device comprising:
a housing comprising a perimeter wall defining a cavity; and
a support structure separating the cavity into a cell chamber and a reservoir chamber, the support structure comprising a nano-channel membrane for fluid communication between the cell chamber and the reservoir chamber, wherein the cell chamber defines a first opening comprising a microstructure; and wherein the nano-channel membrane defines a surface area that is at least 50% of a total surface area of the support structure and the device has a diameter from 8 mm to 25 mm and a thickness from 2.5 mm to 8.0 mm.

* * * * *